United States Patent
Roh et al.

(10) Patent No.: US 11,464,650 B1
(45) Date of Patent: Oct. 11, 2022

(54) SYNCHRONIZED PLACEMENT OF SURGICAL IMPLANT HARDWARE

(71) Applicant: IX Innovation LLC, Seattle, WA (US)

(72) Inventors: Jeffrey Roh, Seattle, WA (US); Justin Esterberg, Mercer Island, WA (US); John Cronin, Jericho, VT (US); Seth Cronin, Essex Junction, VT (US); Michael John Baker, Georgia, VT (US)

(73) Assignee: IX Innovation LLC, Seattle, WA (US)

(*) Notice: Subject to any disclaimer, the term of this patent is extended or adjusted under 35 U.S.C. 154(b) by 0 days.

(21) Appl. No.: 17/495,462

(22) Filed: Oct. 6, 2021

(51) Int. Cl.
| | |
|---|---|
| *A61B 34/32* | (2016.01) |
| *A61B 34/10* | (2016.01) |
| *A61F 2/46* | (2006.01) |
| *G16H 20/40* | (2018.01) |
| *G06F 30/20* | (2020.01) |
| *G16H 40/63* | (2018.01) |

(52) U.S. Cl.
CPC .............. *A61F 2/46* (2013.01); *A61B 34/32* (2016.02); *G06F 30/20* (2020.01); *G16H 20/40* (2018.01); *G16H 40/63* (2018.01); *A61B 2034/105* (2016.02); *A61F 2002/4633* (2013.01)

(58) Field of Classification Search
CPC .. A61B 34/32; A61B 2034/105; G16H 20/40; G16H 40/63; G06F 30/20; A61F 2002/4633
See application file for complete search history.

(56) References Cited

U.S. PATENT DOCUMENTS

| | | | | |
|---|---|---|---|---|
| 2011/0275957 A1* | 11/2011 | Bhandari | ............... | A61B 34/20 600/595 |
| 2014/0135791 A1* | 5/2014 | Nikou | ..................... | A61B 34/30 606/130 |
| 2018/0014891 A1* | 1/2018 | Krebs | ..................... | A61B 17/15 |
| 2019/0000561 A1* | 1/2019 | Decker | ................... | A61B 34/30 |
| 2019/0029765 A1* | 1/2019 | Crawford | ............ | A61B 90/361 |
| 2019/0167356 A1* | 6/2019 | Britton | ................... | A61B 90/50 |
| 2019/0290361 A1* | 9/2019 | Shalayev | ............... | A61B 34/10 |

* cited by examiner

*Primary Examiner* — Kevin T Truong
*Assistant Examiner* — Diana Jones
(74) *Attorney, Agent, or Firm* — Perkins Coie LLP

(57) ABSTRACT

Methods, apparatuses, and systems for robotic insertion of a screw, a rod, or another component of a surgical implant into a patient are disclosed. Synchronous insertion of screws is performed by multiple surgical robots or a single surgical robot having multiple arms and end effectors. The movements of each robotic arm are coordinated into position in preparation of the insertion of multiple surgical implant components at the same time or in the same surgical step. The insertion of the surgical implant components is performed while monitoring the insertion progress. The insertion is completed autonomously or in coordination with a surgeon.

20 Claims, 11 Drawing Sheets

| Action ID | Action | Action Order | Robotic Arm | Implant ID | Patient ID | Age | Gender | Screw Depth (in.) | Rotational Speed (RPM) | Axial Force (PSI) |
|---|---|---|---|---|---|---|---|---|---|---|
| INS-SCRW-0321 | Insert Screw | 25 | A | SF-00345 | 32163 | 35 | Male | 1.5 | 15 | 4 |
| INS-SCRW-0322 | Insert Screw | 25 | B | SF-00345 | 32163 | 35 | Male | 1.5 | 20 | 4 |
| INS-SCRW-0845 | Insert Screw | 31 | A | SF-02345 | 35468 | 64 | Male | 1.75 | 18 | 4 |
| INS-SCRW-0846 | Insert Screw | 31 | B | SF-02345 | 35468 | 64 | Male | 2 | 16 | 5 |
| INS-SCRW-1654 | Insert Screw | 24 | A | SF-10345 | 13254 | 54 | Female | 1.5 | 13 | 6 |
| INS-SCRW-1655 | Insert Screw | 24 | B | SF-10345 | 13254 | 54 | Female | 1.5 | 14 | 7 |
| INS-SCRW-1356 | Insert Screw | 29 | A | SF-02348 | 23546 | 47 | Female | 1.25 | 5 | 3 |
| INS-SCRW-1357 | Insert Screw | 29 | B | SF-02348 | 23546 | 47 | Female | 1 | 5 | 4 |
| INS-SCRW-0645 | Insert Screw | 36 | A | SF-00034 | 34658 | 25 | Male | 1.5 | 9 | 6 |
| INS-SCRW-0646 | Insert Screw | 36 | B | SF-00034 | 34658 | 25 | Male | 1.75 | 8 | 5 |
| INS-SCRW-0816 | Insert Screw | 28 | A | SF-00215 | 20314 | 38 | Male | 2 | 12 | 5 |
| INS-SCRW-0817 | Insert Screw | 28 | B | SF-00215 | 20314 | 38 | Male | 2 | 12 | 4 |

*FIG. 7*

SYNCHRONIZED PLACEMENT OF SURGICAL IMPLANT HARDWARE

TECHNICAL FIELD

The present disclosure is generally related to automated and robotic surgical procedures and specifically to systems and methods for the synchronization of multiple robotic arms and synchronized placement of surgical implant hardware.

BACKGROUND

More than 200 million surgeries are performed worldwide each year, and recent reports reveal that adverse event rates for surgical conditions remain unacceptably high, despite traditional patient safety initiatives. Adverse events resulting from surgical interventions can be related to errors occurring before or after the procedure as well as technical surgical errors during the operation. For example, adverse events can occur due to (i) breakdown in communication within and among the surgical team, care providers, patients, and their families; (ii) delay in diagnosis or failure to diagnose; and (iii) delay in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the health care team. However, conventional methods are typically insufficient to prevent surgical errors and adverse events during surgery.

BRIEF DESCRIPTION OF THE DRAWINGS

FIG. 7 is a table illustrating an example surgical procedure database, in accordance with one or more embodiments.

DETAILED DESCRIPTION

Figure 1:
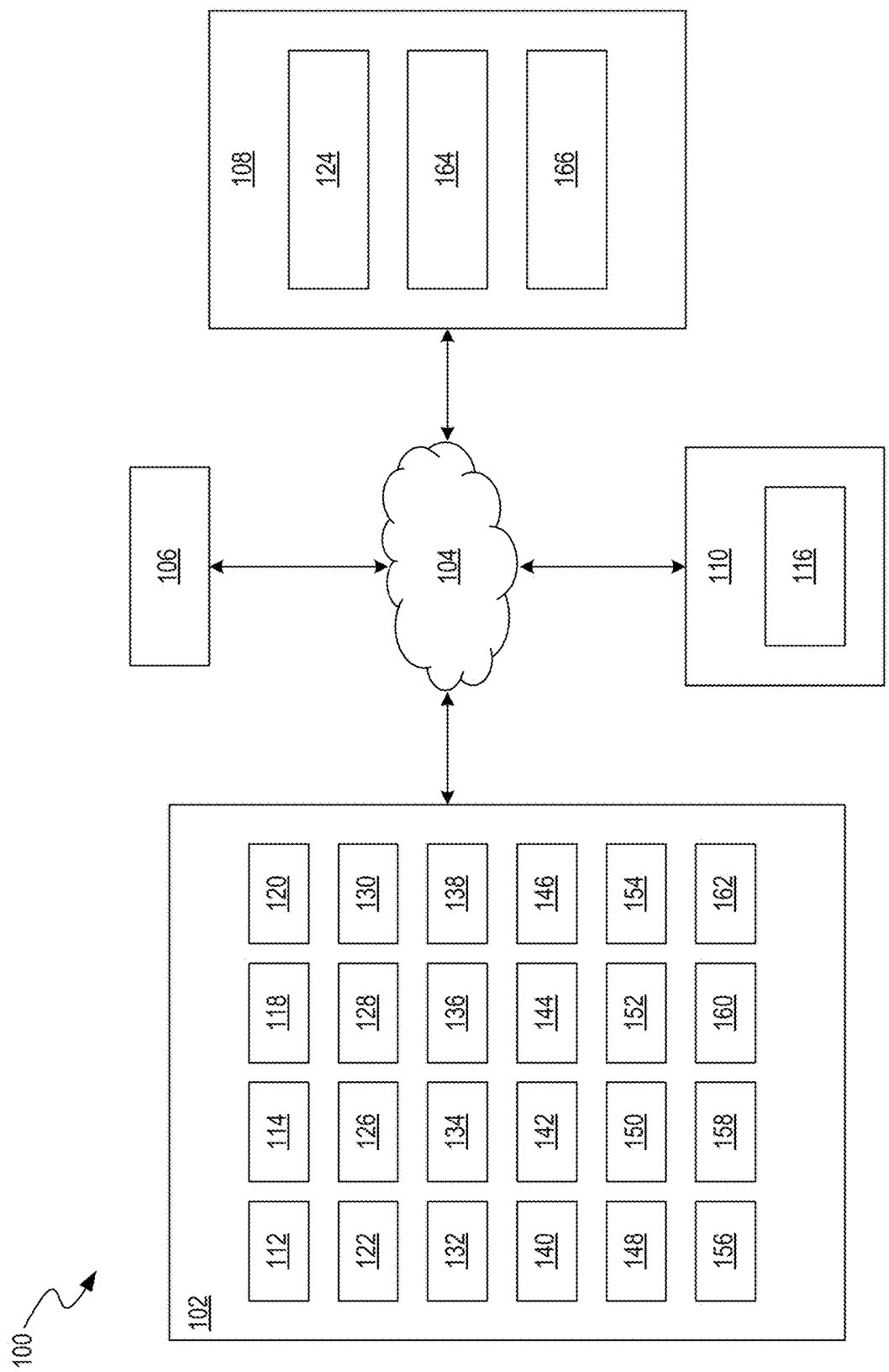
FIG. 1 is a block diagram illustrating an example surgical system, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples. Throughout this specification, plural instances (e.g., "602") may implement components, operations, or structures (e.g., "602a") described as a single instance. Further, plural instances (e.g., "602") refer collectively to a set of components, operations, or structures (e.g., "602a") described as a single instance. The description of a single component (e.g., "602a") applies equally to a like-numbered component (e.g., "602b") unless indicated otherwise. These and other aspects, features, and implementations can be expressed as methods, apparatus, systems, components, program products, means or steps for performing a function, and in other ways. These and other aspects, features, and implementations will become apparent from the following descriptions, including the claims.

A surgical implant refers to a medical device manufactured to replace a missing biological structure, support a damaged biological structure, or enhance an existing biological structure. Some surgical procedures, particularly the implantation of therapeutic devices can require synchronized actions. Traditionally, these surgical procedures have required multiple surgeons to coordinate their human actions, that is, if there was enough space for both surgeons to operate at the same time. Coordinating computerized systems is challenging as it requires synchronizing their internal clocks, which are rarely identical. This is most frequently managed by reducing the clock speed of the more performant controller to that of the less performant controller. Such a process, however, requires a complex configuration and does not allow for the easy setup and replacement of components. Moreover, a surgeon may require additional assistance from a surgical robotic platform while manually performing an operation. The traditional process typically requires another surgeon or technician to operate another surgical robot separate from the surgeon.

The embodiments disclosed herein describe methods, apparatuses, and systems for synchronized placement of surgical implant hardware. In some embodiments, synchronized insertion of surgical implant components for correct patient body positioning is performed. In some embodiments, paths for surgical tools or surgical implant components are selected based on coordinated timing. In some embodiments, in vivo implant assembly is performed using robot arms to access an implantation site using different cannulas (bilateral spine procedures). In some embodiments, the movement of multiple robots (rather than simply robotic arms of the same robot) is coordinated.

The advantages and benefits of the methods, systems, and apparatus disclosed herein include compatibility with best practice guidelines for performing surgery in an operating room, e.g., from regulatory bodies and professional standards organizations such as the Association for Surgical Technologists. The robotic surgical system disclosed coordinates the actions of multiple surgery robots or a single surgery robot having multiple robotic arms to perform coordinated actions within a confined space. The embodiments disclosed improve the setup, configuration, and interoperability of robotic systems to allow multiple robotic arms operated by multiple controllers to synchronize their operations. Moreover, the actions of the surgical robots are coordinated without the need for an additional surgeon or technician; the robotic surgical system disclosed can perform actions based upon the workflow and prompts from a single surgeon. The embodiments provide the ability to coordinate the operation of multiple surgical robots or robotic arms in synchrony, allowing for more complex surgical procedures, particularly in minute locations. A significant benefit provided is obviating the presence of multiple surgeons, thus increasing the number of surgeries that can be performed by a smaller number of surgeons. Further, costs are reduced by reducing the number of personnel who need to be present to complete a surgery. The ability to complete surgical steps at the same time also reduces stress on the patient's body when installing surgical implants since forces can be evenly distributed along a surgical implant at different times, thus reducing the risk of medical complications during a surgical procedure.

The robotic surgery technologies disclosed further offer valuable enhancements to medical or surgical processes through improved precision, stability, and dexterity. The disclosed methods relieve medical personnel from routine tasks and make medical procedures safer and less costly for patients. The embodiments disclosed enable performing more accurate surgery in more minute locations on or within the human body. The embodiments also and address the use of dangerous substances. The adoption of robotic systems, according to the embodiments disclosed herein, provides several additional benefits, including efficiency and speed improvements, lower costs, and higher accuracy. The equipment tracking system integrated into the disclosed embodiments offers flexibility and other advantages, such as requiring no line-of-sight, reading multiple radio frequency identification (RFID) objects at once, and scanning at a distance. The advantages offered by the surgical tower according to the embodiments disclosed herein are smaller incisions, less pain, lower risk of infection, shorter hospital stays, quicker recovery time, less scarring, and reduced blood loss. The advantages of the convolutional neural network (CNN) used for machine learning (ML) in the disclosed embodiments include the obviation of feature extraction and the use of shared weight in convolutional layers, which means that the same filter (weights bank) is used for each node in the layer; this both reduces memory footprint and improves performance.

FIG. 1 is a block diagram illustrating an example surgical system 100, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The console 108 is the same as or similar to the console 420 illustrated and described in more detail with reference to FIG. 4A. The system 100 is implemented using the components of the example computer system 300 illustrated and described in more detail with reference to FIG. 3. Likewise, embodiments of the system 100 can include different and/or additional components or can be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or outpatient surgery center.

In some embodiments, the system 100 includes one or more medical or surgical patient monitors 112. The monitors 112 can include a vital signs monitor (a medical diagnostic instrument), which can be a portable, battery powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiologic parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end tidal CO2 monitor or capnography monitor used for measurement of the level of carbon dioxide that is released at the end of an exhaled breath (referred to as end tidal carbon dioxide, ETCO2). An end tidal CO2 monitor or capnography monitor is widely used in anesthesia and intensive care. ETCO2 can be calculated by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end tidal CO2 monitor can be configured as side stream (diverting) or mainstream (non-diverting). A diverting end tidal CO2 monitor transports a portion of a patient's respired gases from the sampling site to the end tidal CO2 monitor while a non-diverting end tidal CO2 monitor does not transport gas away. Also, measurement by the end tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in artery, used in the operating room 102) for measurement. The non-invasive method (referred to as a sphygmomanometer) works by measurement of force exerted against arterial walls during ventricular systole (i.e., systolic blood pressure occurs when the heart beats and pushes blood through the arteries) and ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate, which is the rate at which breathing occurs, and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can bring a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia where the heart rate becomes faster and bradycardia where the heart rate becomes slower), coronary heart disease, heart attacks, or cardiomyopathy. The instrument used for measurement of the electrocardiogram is called an electrocardiograph which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which help in guiding the surgeon during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP), the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 112 provide electromyography (EMG), the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation, and does not perform external stimulation. Spontaneous EMG is recorded by the insertion of a needle electrode. Triggered EMG refers to the recording of myoelectric signals during stimulation of a target site such as pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end effectors, cameras mounted to the ceiling or other surface above the surgical theater, or cameras mounted on a tripod or other independent mounting device. In some embodiments, the cameras are body worn by a surgeon or other surgical staff, cameras are incorporated into a wearable device, such as an augmented reality device like Google Glass™, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by performing a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. The doctor moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgeon makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals over long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors comprise a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or LEDs. Surgical lights 122 include sterilizable handles which allow the surgeon to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engages with one another. When a telescope is used to operate on the abdomen, the procedure is called laparoscopy. The surgical tower 128 typically includes access to a variety of surgical tools, such as, for example, electrocautery, radiofrequency, lasers, sensors, etc.

In some embodiments, radiofrequency (RF) is used in association with MIS devices. The RF can be used for the treatment of skin by delivering it to the skin through a minimally invasive surgical tool (e.g., fine needles) which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels which are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument can 130 consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools and minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of surgical tool—tissue interaction forces. During MIS, the field of view and workspace of surgical tools are compromised due to the indirect access to the anatomy and lack of surgeon's hand-eye coordination. The sensors 134 provide a tactile sensation to the surgeon by providing information of shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, magnetic resonance imaging (MRI), ultrasound, endoscopy, elastography, tactile imaging, thermography, medical photography, and nuclear medicine, e.g., positron emission tomography (PET). Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used can be brain/spinal cord anomalies, tumors in the body, breast cancer screening, joint injuries, uterine/pelvic pain detection, or heart problems. For the creation of the image by an MRI instrument, magnetic resonance is produced by powerful magnets which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI can more widely suit for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses computed tomography imaging (CT) that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"—of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer which produces sound waves and sends them into the body. The sound waves that are reflected are converted into electrical signals which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for the fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgeons in the placement of specialized surgical instruments and implants. The patient images are taken to guide the physician before or during the medical procedure. The stereotactic navigation system 138 includes a camera having infrared sensors to determine the location of the tip of the probe being used in the surgical procedure. This information is sent in real-time so that the surgeons have a clear image of the precise location where they are working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient and filters out expiratory carbon dioxide. The anesthesiology machine 140 can perform functions such as providing oxygen (O2), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform; flex, or extend individual components of the platform; or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a post-operative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 100 includes a Jackson frame 144 (or Jackson table), which refers to a frame or table which is designed for use in spinal surgeries and can be used in a variety of spinal procedures in supine, prone, or lateral positions in a safe manner. Two peculiar features of the Jackson table 144 are no central table support and an ability to rotate the table through 180 degrees. The Jackson table 144 is supported at both ends which keeps the whole of the table free. This allows the visualization of a patient's trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (sometimes referred to as a Bair™ or Bair Hugger™). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets which cover the patient. The blanket can be designed to use pressure points on the patient's body to prevent heat from reaching areas at risk for pressure sores or burns. The blanket can also include drain holes where fluid passes through the surface of the blanket to linen underneath which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The sequential compression device 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors which can contribute to poor quality in the environment of the operating room 102 are temperature, ventilation, and humidity, and those conditions can lead to profound effects on the health and work productivity of people in the operating room 102. As an example: surgeons prefer a cool, dry climate since they work in bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter. High-Efficiency Particulate Air filter (HEPA filter) protects from infection and contamination by a filter which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The surgical tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system which controls the muscles). A major percentage of orthopedic tools are made of plastic. The orthopedic tools can be divided into the following specialties: hand and wrist, foot and ankle, shoulder and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a surgical tool designed to gradually correct a deformity, e.g., corsets, splints, orthopedic footwear, insoles, and other devices to correct abnormal positions of the foot. A compression-distraction tool refers to a surgical tool designed to correct acquired or congenital deformities of the extremities, e.g., curvature, shortening, and pseudarthrosis such as Gudushauri. A fixation tool can be an internal fixation tool (e.g., screws, plates) or external fixation tools used to correct a radius or tibia fracture. The orthopedic tools can be bone-holding forceps, drill bits, nail pins, hammers, staples, etc.

In some embodiments, the surgical tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can comprise a physical drill, power cord, electronically motorized bone drill, or rotating bone shearing incision work unit.

In some embodiments, the surgical tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be of type absorbable (the stitches automatically break down harmlessly in the body over time without intervention) and non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the surgical tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, surgical tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as sensor/transducer, signal conditioner, display, data storage unit, etc. In some embodiments, the medical equipment includes a sensor to receive a signal from a measurand/patient; a transducer for converting one form of energy to electrical energy; a signal conditioner such as an amplifier, filter, etc., to convert the output from the transducer into an electrical value; a display to provide a visual representation of the measured parameter or quantity; and a storage system to store data which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. A ventilator is required when a person is not able to breathe on their own. A ventilator can perform a function of gently pushing air into the lungs and allows it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc.

The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor which generates a continuous stream of pressurized air which travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. CPAP instrument can comprise a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment 102. The consumables 158 can include gloves, gowns, masks, syringes, needles, sutures, staples, tubing, catheters, or adhesives for wound dressing, in addition to other surgical tools needed by doctors and nurses to provide care. Depending on the device, mechanical testing can be carried out in tensile, compression, or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries are performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light-illuminated and the image seen with the microscope 116 is two-dimensional), dissection or stereoscope (light-illuminated and the image seen with the microscope 116 is three-dimensional), confocal (laser-illuminated and the image seen with the microscope 116 is on a digital computer screen), scanning electron (SEM) (electron-illuminated and the image seen with the microscope 116 is in black and white), or transmission electron microscope (TEM) (electron-illuminated and the image seen with the microscope 116 is the high magnification and high resolution).

The system 100 includes an electronic health records (EHR) database 106 that contains patient records. The EHR are a digital version of patients' paper charts. The EHR database 106 can contain more information than a traditional patient chart, including, but not limited to, a patients' medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker, etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

Figure 2:
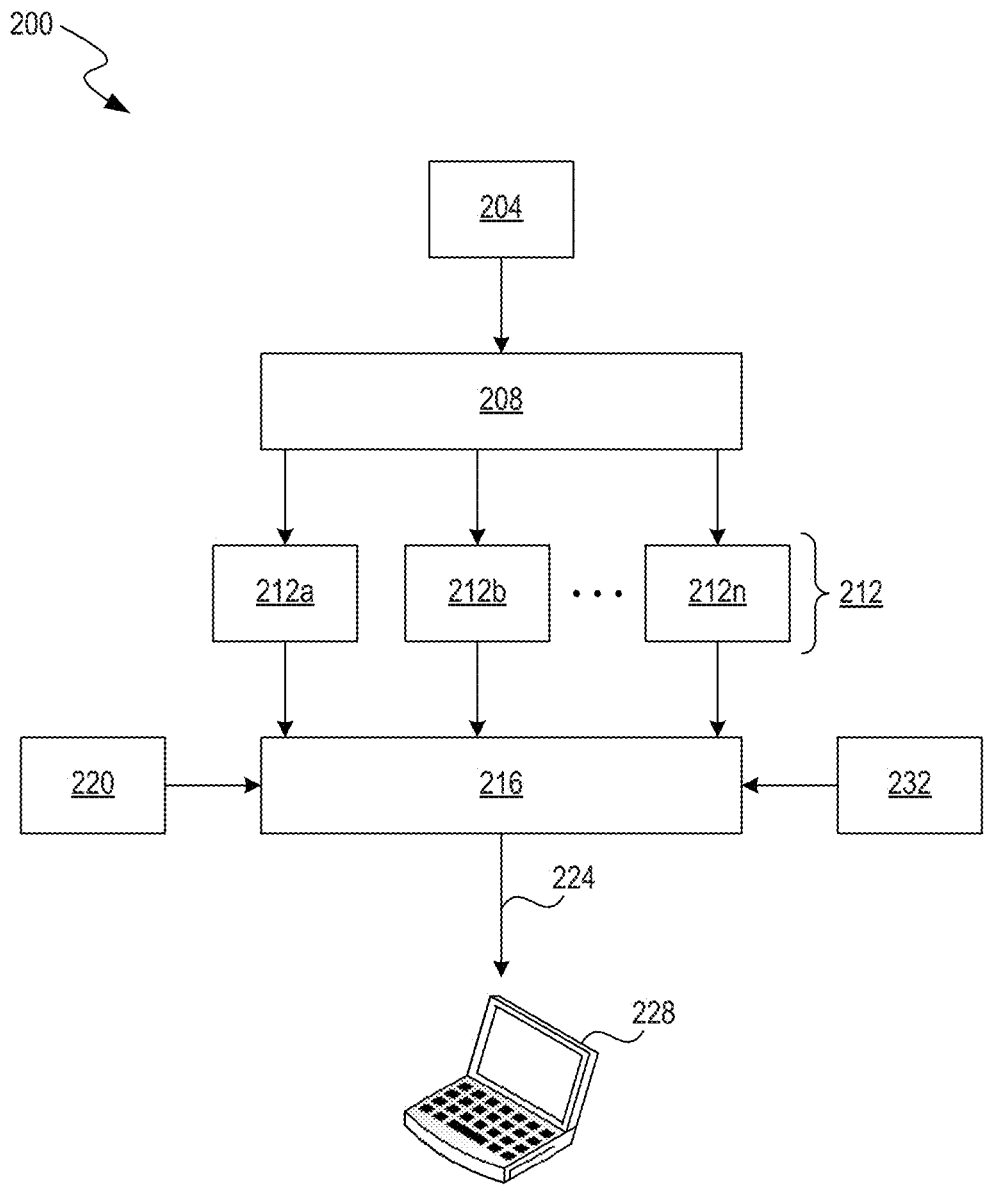
FIG. 2 is a block diagram illustrating an example machine learning (ML) system, in accordance with one or more embodiments.

FIG. 2 is a block diagram illustrating an example machine learning (ML) system 200, in accordance with one or more embodiments. The ML system 200 is implemented using components of the example computer system 300 illustrated and described in more detail with reference to FIG. 3. For example, the ML system 200 can be implemented on the console 108 using instructions programmed in the memory 164 illustrated and described in more detail with reference to FIG. 1. Likewise, embodiments of the ML system 200 can include different and/or additional components or be connected in different ways. The ML system 200 is sometimes referred to as a ML module.

The ML system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, ..., 212n. The feature extraction module 208 reduces the redundancy in the input data 204, e.g., repetitive data values, to transform the input data 204 into the reduced set of features 212, e.g., features 212a, 212b, ..., 212n. The feature vector 212 contains the relevant information from the input data 204, such that events or data value thresholds of interest can be identified by the ML model 216 by using this reduced representation. In some example embodiments, the following dimensionality reduction techniques are used by the feature extraction module 208: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the ML system 200. For example, the ML model 216 can use a cascade of multiple layers of nonlinear processing units for implicit feature extraction and transformation. Each successive layer uses the output from the previous layer as input. The ML model 216 can thus learn in supervised (e.g., classification) and/or unsupervised (e.g., pattern analysis) modes. The ML model 216 can learn multiple levels of representations that correspond to different levels of abstraction, wherein the different levels form a hierarchy of concepts. In this manner, the ML model 216 can be configured to differentiate features of interest from background features.

In alternative example embodiments, the ML model 216, e.g., in the form of a CNN generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker, etc., implemented using components of the example computer system 300 illustrated and described in more detail with reference to FIG. 3. In some embodiments, the steps performed by the ML system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted region of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 216 can be a CNN that includes both convolutional layers and max pooling layers. The architecture of the ML model 216 can be "fully convolutional," which means that variable sized sensor data vectors can be fed into it. For all convolutional layers, the ML model 216 can specify a kernel size, a stride of the convolution, and an amount of zero padding applied to the input of that layer. For the pooling layers, the model 216 can specify the kernel size and stride of the pooling.

In some embodiments, the ML system 200 trains the ML model 216, based on the training data 220, to correlate the feature vector 212 to expected outputs in the training data 220. As part of the training of the ML model 216, the ML system 200 forms a training set of features and training labels by identifying a positive training set of features that have been determined to have a desired property in question, and, in some embodiments, forms a negative training set of features that lack the property in question.

The ML system 200 applies ML techniques to train the ML model 216, that when applied to the feature vector 212, outputs indications of whether the feature vector 212 has an associated desired property or properties, such as a probability that the feature vector 212 has a particular Boolean property, or an estimated value of a scalar property. The ML system 200 can further apply dimensionality reduction (e.g., via linear discriminant analysis (LDA), PCA, or the like) to reduce the amount of data in the feature vector 212 to a smaller, more representative set of data.

The ML system 200 can use supervised ML to train the ML model 216, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The ML system 200 applies the trained ML model 216 to the features of the validation set 232 to quantify the accuracy of the ML model 216. Common metrics applied in accuracy measurement include: Precision and Recall, where Precision refers to a number of results the ML model 216 correctly predicted out of the total it predicted, and Recall is a number of results the ML model 216 correctly predicted out of the total number of features that had the desired property in question. In some embodiments, the ML system 200 iteratively re-trains the ML model 216 until the occurrence of a stopping condition, such as the accuracy measurement indication that the ML model 216 is sufficiently accurate, or a number of training rounds having taken place.

Figure 3:
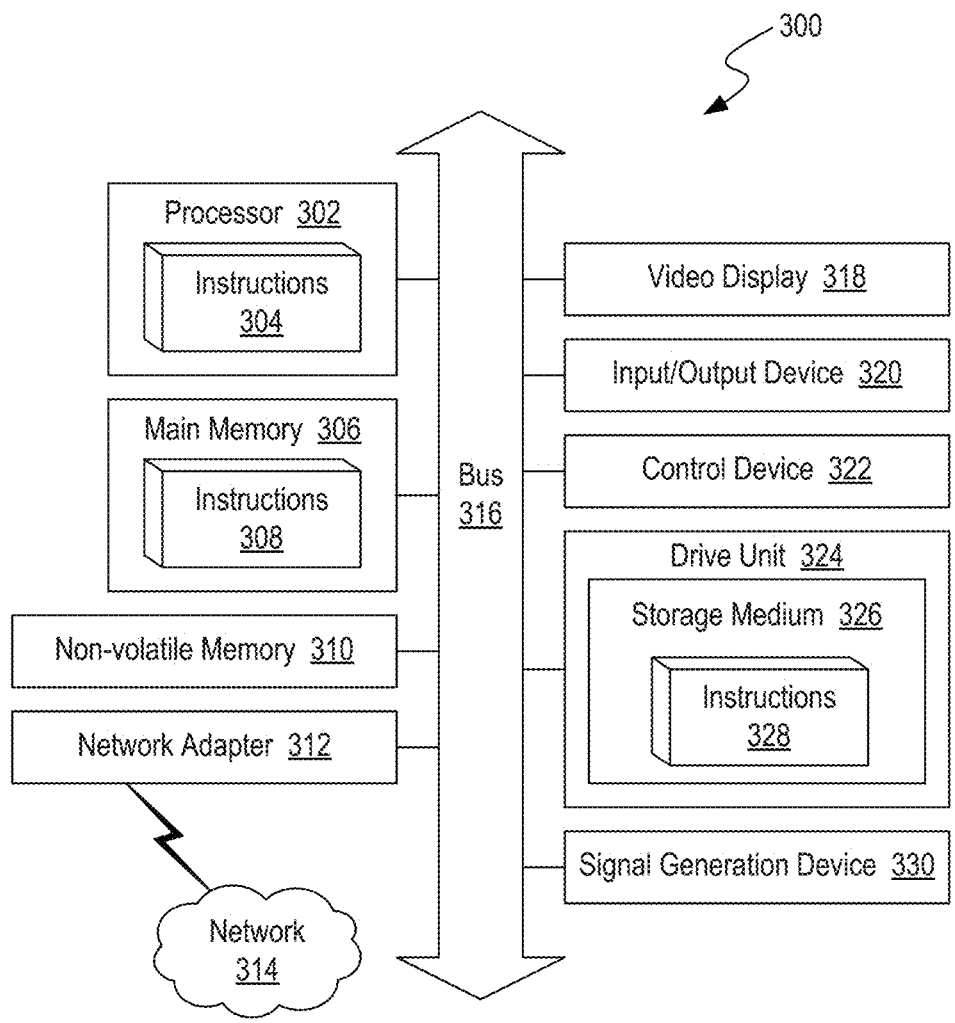
FIG. 3 is a block diagram illustrating an example computer system, in accordance with one or more embodiments.

FIG. 3 is a block diagram illustrating an example computer system, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the ML system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multi-layer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4A:
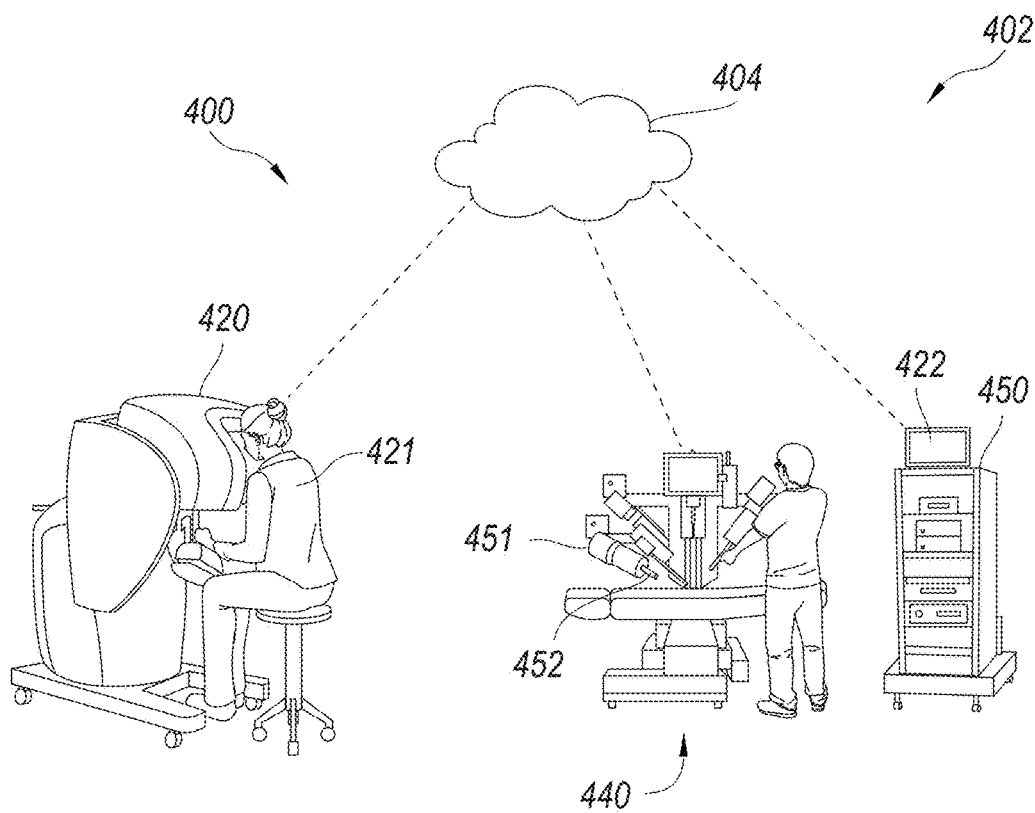
FIG. 4A is a block diagram illustrating an example robotic surgical system, in accordance with one or more embodiments.

FIG. 4A is a block diagram illustrating an example robotic surgical system 400, in accordance with one or more embodiments. The robotic surgical system 400 is the same as or similar to the robotic surgical system 160 illustrated and described in more detail with reference to FIG. 1. The robotic surgical system 400 can include components and features discussed in connection with FIGS. 1-3 and 4B-5. For example, the robotic surgical system 400 can include a console 420 with features of the console 108 of FIG. 1. Likewise, the components and features of FIG. 4A can be included or used with other embodiments disclosed herein. For example, the description of the input devices of FIG. 4A applies equally to other input devices (e.g., input devices 166 of FIG. 1).

The robotic surgical system 400 includes a user device or console 420 ("console 420"), a surgical robot 440, and a computer or data system 450. The console 420 can be operated by a surgeon and can communicate with components in an operating room 402, remote devices/servers, a network 404, or databases (e.g., database 106 of FIG. 1) via the network 404. The robotic surgical system 400 can include surgical control software and can include a guidance system (e.g., ML guidance system, AI guidance system, etc.), surgical planning software, event detection software, surgical tool software, etc. or other features disclosed herein to perform surgical step(s) or procedures or implement steps of processes discussed herein.

The user 421 can use the console 420 to view and control the surgical robot 440. The console 420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 420 can include a clutch pedal to allow the user 421 to disengage one or more sensor-actuator components from control by the surgical robot 440. The console 420 can also include display or output so that the one of more users can observe the patient being operated on, or the product being assembled, for example. In some embodiments, the display can show images, such as, but not limited to medical images, video, etc. For surgical applications, the images could include, but are not limited to, real-time optical images, real-time ultrasound, real-time OCT images and/or other modalities, or could include pre-operative images, such as MRI, CT, PET, etc. The various imaging modalities can be selectable, programmed, superimposed and/or can include other information superimposed in graphical and/or numerical or symbolic form.

The robotic surgical system 400 can include multiple consoles 420 to allow multiple users to simultaneously or sequentially perform portions of a surgical procedure. The term "simultaneous" herein refers to actions performed at the same time or in the same surgical step. The number and configuration of consoles 420 can be selected based on the surgical procedure to be performed, number and configurations of surgical robots, surgical team capabilities, or the like.

Figure 4B:
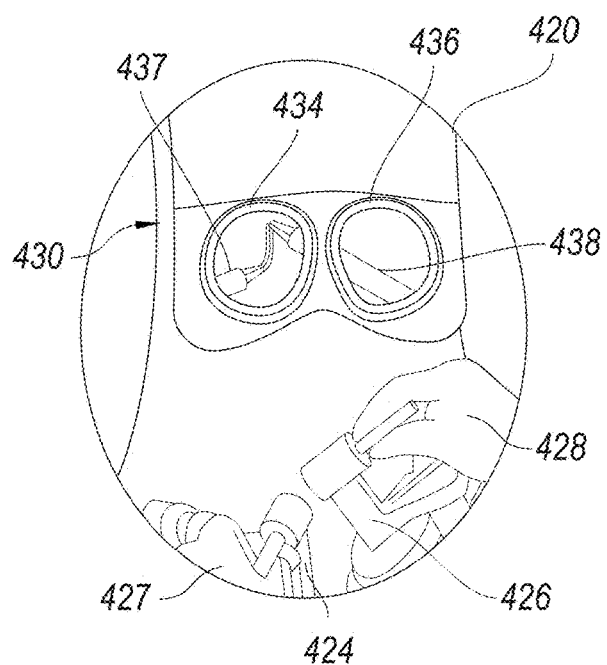
FIG. 4B illustrates an example console of the robotic surgical system of FIG. 4A, in accordance with one or more embodiments.

FIG. 4B illustrates an example console 420 of the robotic surgical system 400 of FIG. 4A, in accordance with one or more embodiments. The console 420 includes hand-operated input devices 424, 426, illustrated held by the user's left and right hands 427, 428, respectively. A viewer 430 includes left and right eye displays 434, 436. The user can view, for example, the surgical site, instruments 437, 438, or the like. The user's movements of the input devices 424, 426 can be translated in real-time to, for example, mimic the movement of the user on the viewer 430 and display (e.g., display 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 420 can be located at the surgical room or at a remote location.

The viewer 430 can display at least a portion of a surgical plan, including past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 430 can be a VR/AR headset, display, or the like. The robotic surgical system 400, illustrated and described in more detail with reference to FIG. 4A, can further include multiple viewers 430 so that multiple members of a surgical team can view the surgical procedure. The number and configuration of the viewers 430 can be selected based on the configuration and number of surgical robots.

Referring again to FIG. 4A, the surgical robot 440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 440 can be selected based on the procedures to be performed.

The surgical robot 440 can operate in different modes selected by a user, set by the surgical plan, and/or selected by the robotic surgical system 400. In some procedures, the surgical robot 440 can remain in the same mode throughout a surgical procedure. In other procedures, the surgical robot 440 can be switched between modes any number of times. The configuration, functionality, number of modes, and type of modes can be selected based on the desired functionality and user control of the robotic surgical system 400. The robotic surgical system 400 can switch between modes based on one or more features, such as triggers, notifications, warnings, events, etc. Different example modes are discussed below. A trigger can be implemented in software to execute a jump to a particular instruction or step of a program. A trigger can be implemented in hardware, e.g., by applying a pulse to a trigger circuit.

In a user control mode, a user 421 controls, via the console 420, movement of the surgical robot 440. The user's movements of the input devices can be translated in real-time into movement of end effectors 452 (one identified).

In a semi-autonomous mode, the user 421 controls selected steps and the surgical robot 440 autonomously performs other steps. For example, the user 421 can control one robotic arm to perform one surgical step while the surgical robot 440 autonomously controls one or more of the other arms to concurrently perform another surgical step. In another example, the user 421 can perform steps suitable for physician control. After completion, the surgical robot 440 can perform steps involving coordination between three or more robotic arms, thereby enabling complicated procedures. For example, the surgical robot 440 can perform steps involving four or five surgical arms, each with one or more end effectors 452.

In an autonomous mode, the surgical robot 440 can autonomously perform steps under the control of the data system 450. The robotic surgical system 400 can be preprogrammed with instructions for performing the steps autonomously. For example, command instructions can be generated based on a surgical plan. The surgical robot 440 autonomously performs steps or the entire procedure. The user 421 and surgical team can observe the surgical procedure to modify or stop the procedure. Advantageously, complicated procedures can be autonomously performed without user intervention to enable the surgical team to focus and attend to other tasks. Although the robotic surgical system 400 can autonomously perform steps, the surgical team can provide information in real-time that is used to continue the surgical procedure. The information can include physician input, surgical team observations, and other data input.

The robotic surgical system 400 can also adapt to the user control to facilitate completion of the surgical procedure. In some embodiments, the robotic surgical system 400 can monitor, via one or more sensors, at least a portion of the surgical procedure performed by the surgical robot 440. The robotic surgical system 400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 400 can perform one or more actions based on the identified event. The actions can include, without limitation, modification of the surgical plan to address the potential adverse surgical event, thereby reducing the risk of the event occurring.

In some embodiments, the robotic surgical system 400 can determine whether a detected event is potentially an adverse surgical event based on one or more criteria set by the robotic surgical system 400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 400 can take other actions in response to identification of an event. If the robotic surgical system 400 identifies an end effector malfunction or error, the robotic surgical system 400 can stop usage of the end effector and replace the malfunctioning component (e.g., surgical tool or equipment) to complete the procedure. The robotic surgical system 400 can monitor hospital inventory, available resources in the surgical room 402, time to acquire equipment (e.g., time to acquire replacement end effectors, surgical tools, or other equipment), and other information to determine how to proceed with surgery. The robotic surgical system 400 can generate multiple proposed surgical plans for continuing with the surgical procedure. The user and surgical team can review the proposed surgical plans to select an appropriate surgical plan. The robotic surgical system 400 can modify a surgical plan with one or more corrective surgical steps based on identified surgical complications, sensor readings, or the like.

The robotic surgical system 400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-site and off-site simulations (e.g., pre- or post-operative virtual simulations, simulations using models, etc.) can be generated and collected.

The surgical robot 440 can include robotic arms 451 (one identified) with integrated or removable end effectors 452 (one identified). The end effectors 452 can include, without limitation, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or surgical tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 440 to provide more intelligent and intuitive results.

The data system 450 can improve surgical planning, monitoring (e.g., via the display 422), data collection, surgical robotics/navigation systems, intelligence for selecting instruments, implants, etc. The data system 450 can execute, for example, surgical control instructions or programs for a guidance system (e.g., ML guidance system, AI guidance system, etc.), surgical planning programs, event detection programs, surgical tool programs, etc. For example, the data system 450 can increase procedure efficiency and reduce surgery duration by providing information insertion paths, surgical steps, or the like. The data system 450 can be incorporated into or include other components and systems disclosed herein.

The robotic surgical system 400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems can be used with many different systems for conducting robotic or minimally invasive surgery. One example of a surgical system and surgical robots which can incorporate methods and technology is the DAVINCI™ system available from Intuitive Surgical, Inc.™ of Mountain View, Calif. However, other surgical systems, robots, and apparatuses can be used.

The robotic surgical system 400 can perform one or more simulations using selected entry port placements and/or robot positions, to allow a surgeon or other user to practice procedures. The practice session can be used to generate, modified, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operative or intraoperatively.

Embodiments can provide a means for mapping the surgical path for neurosurgery procedures that minimize damage through artificial intelligence mapping. The software for artificial intelligence is trained to track the least destructive pathway. The physician can make an initial incision based on a laser marking on the skin that illuminates the optimal site. Next, a robot can make a small hole and insert surgical equipment (e.g., guide wires, cannulas, etc.) that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and posttreatment mapping can be compared by the surgeon and/or ML/AI system. The comparison can be used to determine next steps in a procedure and/or further train the ML/AI system.

Figure 5:
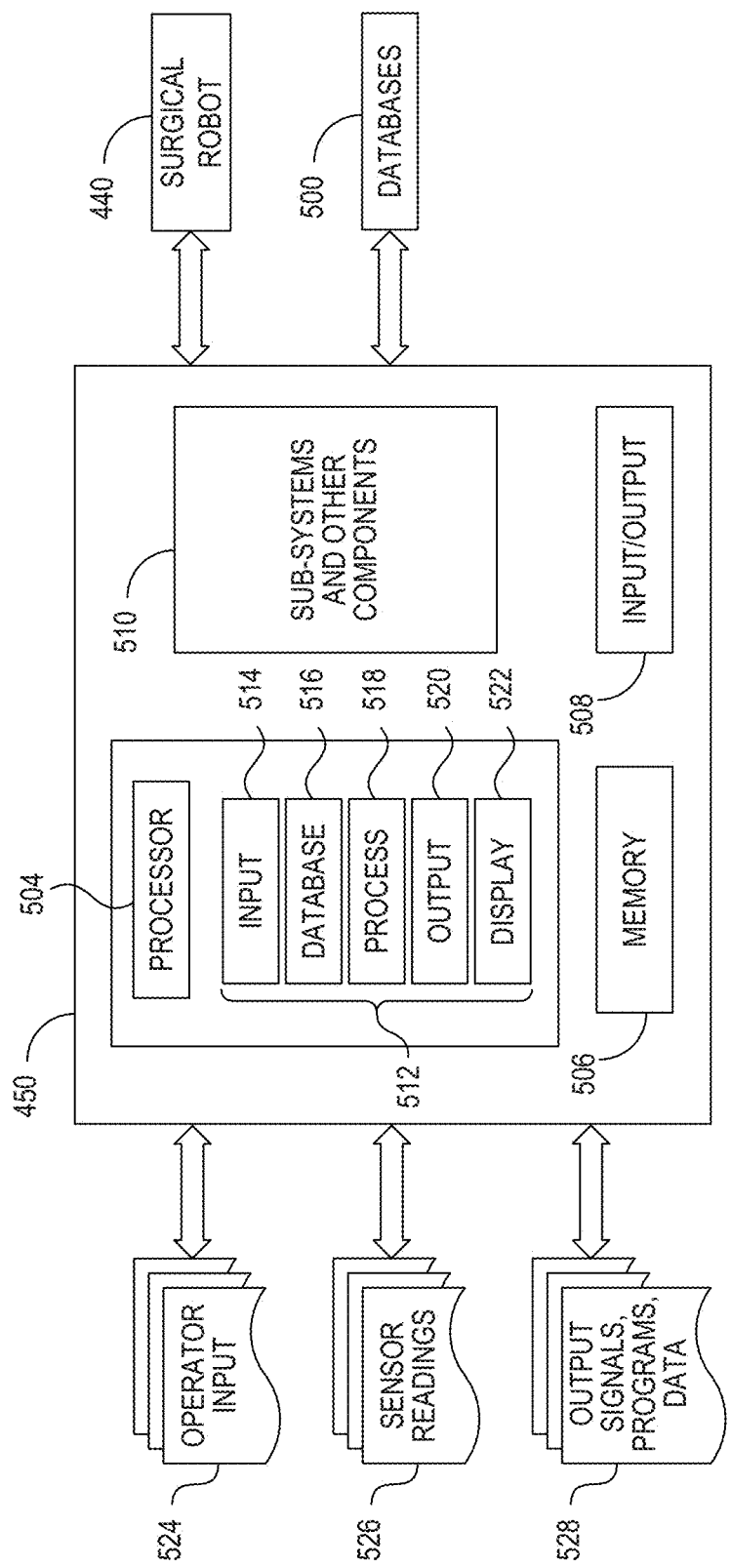
FIG. 5 is a schematic block diagram illustrating subcomponents of the robotic surgical system of FIG. 4A, in accordance with one or more embodiments.

FIG. 5 is a schematic block diagram illustrating subcomponents of the robotic surgical system 400 of FIG. 4A in accordance with embodiment of the present technology. The data system 450 has one or more processors 504, a memory 506, input/output devices 508, and/or subsystems and other components 510. The processor 504 can perform any of a wide variety of computing processing, image processing, robotic system control, plan generation or modification, and/or other functions. Components of the data system 450 can be housed in a single unit (e.g., within a hospital or surgical room) or distributed over multiple, interconnected units (e.g., though a communications network). The components of the data system 450 can accordingly include local and/or devices.

As illustrated in FIG. 5, the processor 504 can include a plurality of functional modules 512, such as software modules, for execution by the processor 504. The various implementations of source code (i.e., in a conventional programming language) can be stored on a computer-readable storage medium or can be embodied on a transmission medium in a carrier wave. The modules 512 of the processor 504 can include an input module 514, a database module 516, a process module 518, an output module 520, and, optionally, a display module 524 for controlling the display.

In operation, the input module 514 accepts an operator input 524 via the one or more input devices, and communicates the accepted information or selections to other components for further processing. The database module 516 organizes plans (e.g., robotic control plans, surgical plans, etc.), records (e.g., maintenance records, patient records, historical treatment data, etc.), surgical equipment data (e.g., instrument specifications), control programs, and operating records and other operator activities, and facilitates storing and retrieving of these records to and from a data storage device (e.g., internal memory 506, external databases, etc.). Any type of database organization can be utilized, including a flat file system, hierarchical database, relational database, distributed database, etc.

In the illustrated example, the process module 518 can generate control variables based on sensor readings 526 from sensors (e.g., end effector sensors of the surgical robot 440, patient monitoring equipment, etc.), operator input 524 (e.g., input from the surgeon console 420 and/or other data sources), and the output module 520 can communicate operator input to external computing devices and control variables to controllers. The display module 522 can be configured to convert and transmit processing parameters, sensor readings 526, output signals 528, input data, treatment profiles and prescribed operational parameters through one or more connected display devices, such as a display screen, touchscreen, printer, speaker system, etc.

In various embodiments, the processor 504 can be a standard central processing unit or a secure processor. Secure processors can be special-purpose processors (e.g., reduced instruction set processor) that can withstand sophisticated attacks that attempt to extract data or programming logic. The secure processors cannot have debugging pins that enable an external debugger to monitor the secure processor's execution or registers. In other embodiments, the system can employ a secure field-programmable gate array, a smartcard, or other secure devices.

The memory 506 can be standard memory, secure memory, or a combination of both memory types. By employing a secure processor and/or secure memory, the system can ensure that data and instructions are both highly secure and sensitive operations such as decryption are shielded from observation. In various embodiments, the memory 506 can be flash memory, secure serial EEPROM, secure field-programmable gate array, or secure application-specific integrated circuit. The memory 506 can store instructions for causing the surgical robot 440 to perform acts disclosed herein.

The input/output device 508 can include, without limitation, a touchscreen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. For example, if an applicator moves an undesirable amount during a treatment session, the input/output device 508 can alert the subject and/or operator via an audible alarm. The input/output device 508 can be a touch screen that functions as both an input device and an output device.

The data system 450 can output instructions to command the surgical robot 440 and communicate with one or more databases 2600. The surgical robot 440 or other components disclosed herein can communicate to send collected data (e.g., sensor readings, instrument data, surgical robot data, etc.) to the database 500. This information can be used to, for example, create new training data sets, generate plans, perform future simulations, post-operatively analyze surgical procedures, or the like. The data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between surgical equipment within the surgical room.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 440. For example, mode switching programs can include threshold or configuration settings for determining when to switch the mode of operation of the surgical robot 440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to optimize patient outcome, reduce or limit the risk of surgical complications, mitigate adverse events, manage costs for surgical procedures, reduce recovery time, or the like. The healthcare provider can modify how plans are generated over time to further optimize based on one or more criteria.

Figure 6:
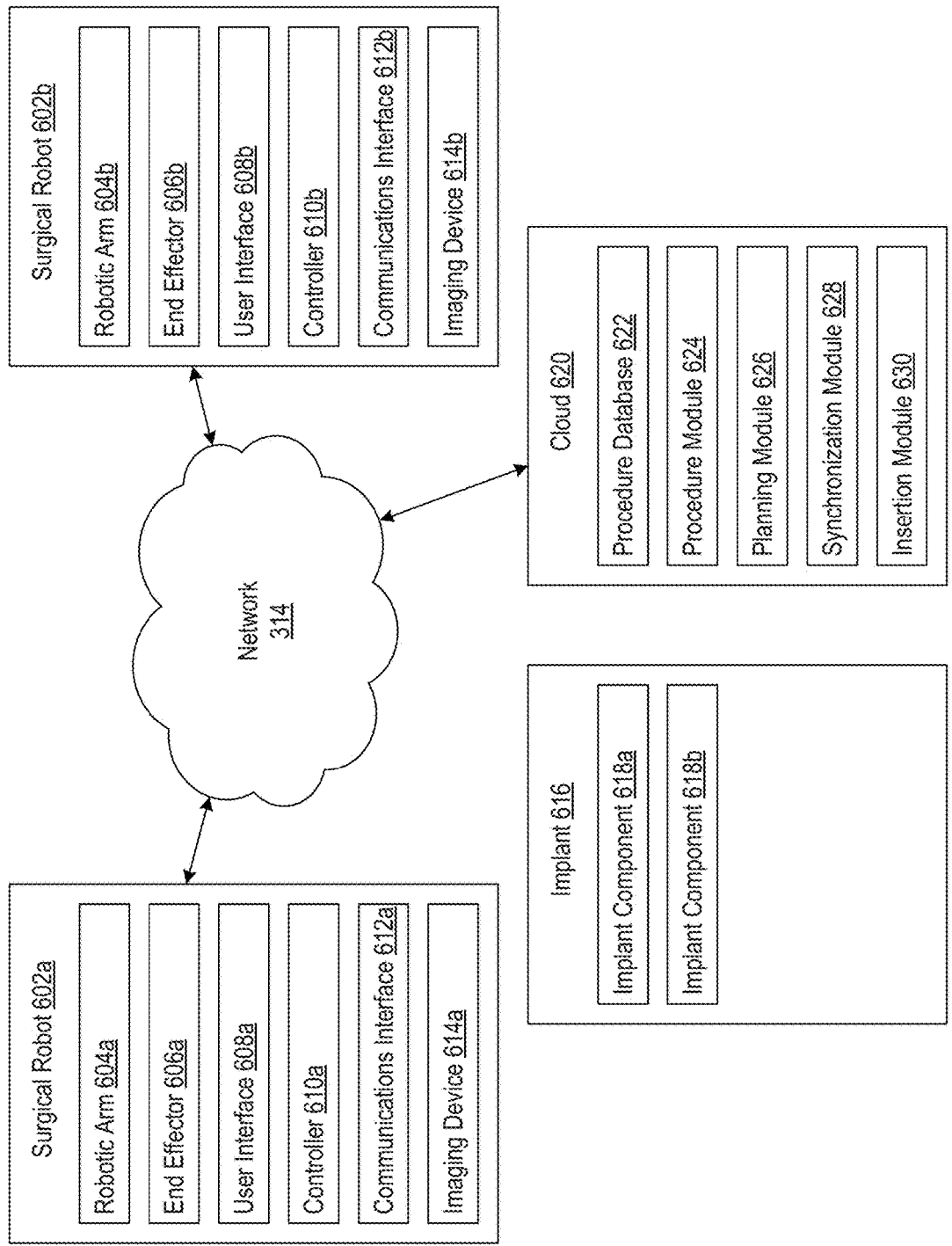
FIG. 6 is a block diagram illustrating an example robotic surgical system for synchronized placement of surgical implant hardware, in accordance with one or more embodiments.

FIG. 6 is a block diagram illustrating an example robotic surgical system for synchronized placement of surgical implant hardware, in accordance with one or more embodiments. The term "synchronous" herein refers to events or actions performed or occurring together or in the same time period. The placement of surgical implants or surgical implant components is sometimes referred to as "implantation," "insertion," or "installation." Alternately, "implantation" can refer to the overall process for installing a surgical implant 616 that includes "inserting" the surgical implant components 168*a*, 618*b*. A robotic action refers to one or more physical movements of a surgical robot (e.g., the surgical robot 602*a*), such as aligning a surgical implant component 618*a* or a surgical tool 154 (see FIG. 1), initiating the rotation of a rotary surgical tool, applying an axial force to a surgical tool 154, etc.

The system of FIG. 6 includes at least one surgical robot (e.g., surgical robot 602*a*), databases and modules that can be implemented in the cloud 620, and at least one surgical implant 616. Each surgical robot is the same as or similar to the surgical robot 440 illustrated and described in more detail with reference to FIG. 4A. The system is implemented using the components of the example computer system 300 illustrated and described in more detail with reference to FIG. 3. Likewise, embodiments of the system can include different and/or additional components or can be connected in different ways.

The robotic surgical system of FIG. 6 includes at least one surgical robot 602a, which is a robotic system designed to assist a surgeon in performing a surgical operation on a patient. Each surgical robot includes at least one controller 610a and at least one robotic arm 604a having an end effector 606a and/or at least one imaging device 614a. In embodiments, both robotic arms 604a, 604b are connected to a single surgical robot 602a. The surgical robots 602a, 602b are different from each other and communicate via the network 314, which is illustrated and described in more detail with reference to FIG. 2. For example, the surgical robot 602a can be used for more-precise maneuvers while the surgical robot 602b is used for less-precise maneuvers, or the end effector 606a is differently shaped than the end effector 606b and used for grasping different tools than the end effector 606b.

Each surgical robot (e.g., the surgical robot 602a) can further include a user interface 608a for accepting control inputs from a user, such as a surgeon or other medical professional, and a communications interface 612a for transmitting and receiving data to and from a cloud 620 for the purpose of training an artificial intelligence (AI). The AI can operate within the surgical robot 602a or receive remote commands from a remote user. The AI can be implemented external to the surgical robot 602b (see FIG. 2). The robotic arm 604a is a mechanically actuated arm or lever having at least two degrees of freedom. The robotic arm 604a typically includes at least one end effector 606a or an imaging device 614a and can include both the end effector 606a and the imaging device 614a. The robotic arm 604a can additionally be capable of changing the end effector 606a to facilitate multiple functions and operation of a variety of tools. The robotic arm 604a can be manually controlled or operated in an autonomous or semi-autonomous mode.

Each surgical robot can have one robotic arm or multiple robotic arms 604, each of which can be operated independently by one or more users or autonomous systems or a combination of users and autonomous systems. In embodiments, both robotic arms 604a, 604b are connected to a single surgical robot 602a. The end effector 606a is the end of the robotic arm 604a that performs work. The end effector 606a is typically a tool or device for interacting with a physical object and can be a surgical tool intended for acting upon or within a patient or a gripping device for securing a separate surgical tool to the robotic arm 604a. The end effector 606a can be permanently affixed to the end of the robotic arm 604a or can be detachable, thus allowing for a system of interchangeable end effectors 606 that can alternatively be selected and swapped by a single robotic arm or multiple robotic arms.

The user interface 608a is a means of interacting with the surgical robot 602a and can include any of a keyboard, computer mouse, trackball, joystick, wireless or wired gamepad, sliders, scroll wheels, touch screen or microphone for receiving voice commands. The user interface 608a can additionally include other methods of interaction of a user with the surgical robot 602a. The user interface 608a can accept direct inputs, such as from a joystick controlling the movement of a robotic arm or indirect inputs such as commands entered on a keyboard or touch screen such as adjusting the sensitivity of a joystick control or the speed of the robotic arm 604a's movement in response to a joystick.

The controller 610a is a computing device including a processor for completing computations and a memory component for storing data for use in computations (see FIG. 3). The memory can store data temporarily, such as for intermediate values used by the controller 610a to complete complex computations or can additionally include persistent storage for longer term storage of information. The controller 610a is in communication with a communications interface 612a and can further be allowed to control at least one robotic arm 604a and end effector 606a of the surgical robot 602a. The communications interface 612a allows the surgical robot 602a to communicate with external devices (e.g., the surgical robot 602b) and can include a wireless antenna and transceiver or a port for receiving a cable to facilitate a wired connection. Examples of a wired connection include ethernet, universal serial bus (USB), or a proprietary connection. A wireless communications interface can include any of Wi-Fi, Bluetooth, near-field communications (NFC), or a cellular communications interface such as 3G, 4G, LTE, or 5G. The communications interface 612a can connect a user interface to the surgical robot 602a, the surgical robot 602b, a local network (e.g., network 314) or the cloud network 620 to access a remote server and/or database.

The at least one imaging device 614a is any device capable of detecting sound or electromagnetic waves and assembling a visual representation of the detected waves. Imaging devices 614 can collect waves from any part of the electromagnetic spectrum or sounds at any range of frequencies, often as a matrix of independently acquired measurements, which each represent a pixel of a two or three-dimensional image. The measurements can be taken at the same time, in the same surgical step, or in series via a scanning process or a combination of methods. Some pixels of an image produced by the imaging devices 614 can be interpolated from direct measurements representing adjacent pixels in order to increase the resolution of the generated image. Imaging devices 614 can receive or generate imaging data from multiple imaging devices (see FIG. 1). The multiple imaging devices can include, for example, cameras attached to the robotic arms 604, cameras mounted to the ceiling or other above the surgical theater, cameras mounted on a tripod or other independent mounting device, cameras that are body worn by the surgeon or other surgical staff, cameras incorporated into a wearable device, such as an augmented reality device (e.g., Google Glass™) cameras that are integrated into an endoscopic, microscopic, laparoscopic, or other imaging device (e.g., ultrasound) present in the surgical theater. The imaging devices 614 can execute an algorithm or software module capable of determining qualitative or quantitative data from medical images, for example, a deep learning algorithm that has been trained on a data set of medical images (see FIG. 2).

The at least one surgical implant 616 is a therapeutic prosthetic device intended to reinforce or restore functionality to a part of a body that has been impacted by an injury, typically traumatic, or a degenerative disease that can result in the loss or destruction of a part of the body. The implant 616 can be rigid, such as when reinforcing bone structures, or flexible, such as when replacing or supplementing soft tissues. Similarly, the implant 616 can be static and unmoving, or can include articulating joints or other moveable elements. The implant 616 can include any of a range of materials, each of which can have different properties, such as being rigid or flexible. Multiple materials can be utilized in different implant components or at a location where implant components meet to perform different functions, thus creating more complex implants. The at least one surgical implant 616 can be a single piece or include multiple implant components. Implants that include multiple implant components can alternatively be referred to as assemblies.

The implant 616 is typically customized to fit a patient and a specific application the implant 616 is intended for. In some embodiments, the implant 616 includes biological donor tissues or biosynthetic tissues, such as can be used in operations, such as organ transplant, skin graft, or other tissue implantation or replacement. In other embodiments, the implant 616 is any of multiple implantable medical devices, for example, spinal devices (e.g., intervertebral cages, artificial disks, rod/screw systems, etc.), cardiac pacemakers, stents, joints (e.g., hip joints, knee joints, etc.), a spinal fusion implant, electric neurological stimulation devices, such as vagus nerve stimulators or deep brain stimulators, blood glucose monitors, insulin pumps, etc. The implant components 618a, 618b are each a single manufacturable component of the surgical implant 616. The implant component 618a or 618b can include subassemblies, such as hinges, balls, or sockets to create joints, or simple components such as screws, rods, plates, and other components, which can be included in the implant 616. The implant component 618b can be customized when it is manufactured, or alternatively, before or during implantation. In some embodiments, the implant 616 includes a plate and screws configured to fix the plate to one or more bones. The robotic rotation of the screws for insertion can be coordinated with the positioning of the plate at a target location. This allows the implant 616 to be assembled within the patient's body. Examples for positioning screws (e.g., inserting screws into an implant component 618a, tissue, etc.) are discussed in connection with FIG. 7.

In some embodiments, the implant 616 includes an expandable intervertebral device and one or more screws (e.g., locking screws, expansion screws, etc.). The first surgical robot 602a can position and expand the intervertebral device within a patient's body, and the second surgical robot 602b can install the screw(s) in the partially or completely expanded intervertebral device, thereby locking the intervertebral device in the desired configuration. In some embodiments, the implant 616 is an artificial disk assembled within an intervertebral space. The implant 616 can include endplates positioned by the first surgical robot 602a and a joint mechanism that can be positioned between the endplates by the second surgical robot 602b. Movement of the robots 602a, 602b can be coordinated to fix the endplates to the joint mechanism before or after the endplates contact vertebral endplates. In some embodiments, a third robot installs couplers that couple the joint mechanism to the endplates. In some embodiments, the implant 616 is a multi-component interspinous spacer device assembled within the patient's body.

An expandable instrument (e.g., a cannula, a conical sleeve, etc.) can be expanded within the patient's body to create an open space for assembling the implant 616. The number of robots, assembly techniques, and configuration of the implant 616 can be selected based on the functionality of the robot(s), implantation plan, and space for assembly within the patient's body. The surgical system can retrieve assembly instructions from an instruction database, manufacture database, or other source. The assembly instructions can provide implantation parameters, position information, alignment information, sequence of steps, etc. The implantation parameters can include insertion parameters (e.g., speed parameters, alignment parameters, etc.), forces (e.g., maximum forces, minimum forces), torque settings (e.g., average torque, maximum torque, installed torque), speed(s) (e.g., rotational speeds, displacement speeds, alarm/warning setting(s)), fits (e.g., press fit, friction fit, interference fit), or the like.

In some embodiments, an implant assembly is partially assembled robotically outside the patient's body and then fully assembled inside the patient's body. Imaging equipment can be used to evaluate the patient's body to determine which assembly steps to perform outside the body or inside the body, assembly locations within the patient's body, etc. In some embodiments, the surgical system determines suitable locations within the patient's body to assemble one or more components. For example, screws can be inserted through holes of a fixation plate within a space in the patient's body. The screw/plate implant can be moved together to an implantation position along the patient's spine. The screws can then be torqued to drive the screws into bone.

The components of the implant 616 can be delivered along different paths into the patient. This allows large implants to be delivered minimally invasively into the patient. In some spinal procedures, a first surgical component of the implant 616 can be delivered through an incision in canula positioned on one side of the patient's sagittal plane. A second surgical component of the implant 616 can be delivered through an incision in canula position on the other side of the sagittal plane. This allows bilateral delivery of the implant components to the implantation site. The implant 616 can have any number of separate components that are assembled inside the patient. In some assembly procedures, the multiple components can be mechanically coupled together using one or more fasteners. During the assembly procedure, a system can monitor the assembly process and identify adverse events using one or more machine learning models. A surgical plan can include multiple assembly procedures that can be adapted based on real-time data collected by the surgical system. This allows the surgical system to analyze data to select a surgical plan, modify selected surgical plans, and detect adverse events.

The systems disclosed herein can assemble implants at an implantation site or at another location within the patient. For implantation site assembly, a robotic system can move components of the implant assembly, which are spaced apart from one another, towards the implantation site. The robotic system can determine the orientation, position, and/or movement of the components to bring them together in a predetermined manner. To assemble implants near the implantation site, the robotic system can assemble the implant and can then move the assembled implant to the implantation site. Further manipulation and adjustments to the implant can be performed as needed. The robotic system can monitor the assembly, positioning, and implantation to determine further modifications based on the surgical plan. One or more virtual simulations can be performed before or during the surgical procedure. The virtual simulations can be used to determine assembly procedures for assembling the implant based on, for example, scoring determined for each of the virtual simulations. The scoring can include determining scores for a time period for performing a surgical step, score for risk of one or more adverse events, score for predicted surgical outcomes, or other suitable scores. The surgical team can set the scoring criteria based on the surgical plan. Scoring algorithms can be used to weigh and select scores that affect the surgical procedure, reduce surgical costs, and improve outcomes.

The cloud 620 is a distributed network of computers including servers and databases. The cloud 620 can be a private cloud, where access is restricted by isolating the network, such as preventing external access or by encryption to limit access to only authorized users. Alternatively, the cloud 620 is a public cloud, where access is widely available via the Internet. A public cloud may not be secured or can include limited security features. The surgical procedure database 622 stores data from previous surgical procedures, such as surgical implant insertion procedures. The data can describe patients, tools and hardware used, previously installed surgical implants and surgical implant components, previous patient outcomes, previous surgical tool paths, previous insertion parameters used for controlling robotic arms or end effectors, and the timing for each action performed during a previous surgical procedure.

The procedure module 624 is used to perform surgical operations utilizing the synchronous operation of multiple robotic arms 604a, 604b and end effectors 606a, 606b, such as in the insertion of screws at the same time or in the same surgical step during the installation of a surgical implant 616. In some embodiments, one or more processors of the surgical system of FIG. 6 generate an implantation plan for implanting the surgical implant 616 in a patient's body. The implantation plan includes insertion parameters for controlling the first surgical robot 602a and the second surgical robot 602b of the surgical system. The surgical implant includes the first surgical implant component 618a and the second surgical implant component 618b. For example, the procedure module 624 receives the implantation plan from the planning module 626.

The procedure module 624 alternatively allows a surgeon to manually perform an action or prompts a synchronization module 628 to synchronize the multiple robotic arms 604 and end effectors 606 of the one or more surgical robots 602 prior to prompting the insertion module 630 to initiate and monitor the insertion of the surgical implant components 618. In some embodiments, the synchronization module 628 is implemented on the cloud 620 as shown by FIG. 6. In other embodiments, the synchronization module 628 is implemented on the first surgical robot 602a or on the second surgical robot 602b. In other embodiments, an instance of the synchronization module 628 is implemented on each of the first surgical robot 602a and the second surgical robot 602b for the two surgical robots 102 to communicate actions, coordinates of movement, timing constraints, etc., to each other as they perform a synchronous action at the same time or in the same surgical step. The synchronized operation of robotic arms 604 and end effectors 606 is not limited to the insertion of surgical implant components 618 but can additionally be used to perform other synchronized actions, such as making incisions, moving tissues, or manipulating tools. The steps included in the implantation plan are performed until none remain and the implantation procedure is complete.

The planning module 126 is used to generate an implantation plan. A patient is imaged using the at least one imaging device 614 either before or during surgery. If imaging is performed during surgery, an implantation plan generated before surgery can be modified based on the new imaging. A virtual model of at least a portion of the patient's body is generated from the images. The virtual model can include the entirety of the patient's body or, alternatively, only a portion of the patient's body. Models of the surgical implant components 618 are placed within the virtual model and surgical tool paths are generated. Example surgical tools 154 are illustrated and described in more detail with reference to FIG. 1. Additionally, insertion parameters are generated that can be used by the insertion module 630 to control the path of a surgical tool 154 or the surgical implant 616, the speed at which the surgical tool 154 moves, the orientation of the surgical implant components 618, or the axial forces to be applied. The insertion parameters can be discrete values or a range of acceptable values. Further, each action, including a surgical tool path and insertion parameters, is assigned to a surgical robot and a robotic arm, and is provided a timing, including both an order in which each action should be completed and a duration, to create a schedule. The resulting schedule is used to generate the implantation plan.

The synchronization module 628 is used to prepare two or more robotic arms 604, which can be controlled by one or more surgical robots 602 for synchronous operation. Each robotic arm is provided its actions, including at least a surgical tool path and insertion parameters. The synchronization module 628 can direct any necessary pre-synchronous or post-synchronous movements or actions, such as aligning the robotic arms 604 and end effectors 606 into the position at which synchronous operation will begin when initiated. The synchronization module 628 terminates execution when the robotic arms 604a, 604b and their end effectors 606a, 606b are properly positioned in a standby state ready to begin synchronous operation. The insertion module 630 controls the insertion of surgical implant components 618 into a patient at the same time or in the same surgical step when prompted by the installation module 624. The insertion module 630 initiates the synchronous insertion of the surgical implant components 618 into the patient while monitoring the insertion parameters measured in real-time to determine whether the parameters are within a range of acceptable insertion parameter values determined by the planning module 626. The insertion parameters may additionally have been pre-approved by a surgeon who may continuously monitor the process. The insertion of the surgical implant components 618 can additionally prompt any other step in the procedure, including making incisions, responding to bleeding, or simply controlling the movement of a surgical tool 154 or imaging device 614b, and does not require a surgical implant component 618 to be involved.

FIG. 7 is a table illustrating an example surgical procedure database 622, in accordance with one or more embodiments. The surgical procedure database 622 (see FIG. 6) stores data from previous surgical procedures, such as previous implant insertion procedures. The data includes previous patient data, hardware used, surgical tool paths, insertion parameters, and timing information for each action taken during the previous surgical procedures. The patient data can include gender, age, height, weight, medical conditions, patient medical history, patient family medical history, allergies, or vital information, such as measurements of heart rate, blood pressure, blood oxygen saturation, or respiration rate. The previous hardware used can include surgical tools 154, end effectors, surgical implants, or surgical implant components as well as intermediary materials such as guides or consumables that were used. The previous actions can include surgical tool paths, parameters, such as insertion parameters for inserting surgical implant components, or timing information specifying the order in which the actions were taken and the duration of each action. The actions can have the same order identifier indicating actions that were taken at the same time or in the same surgical step. The actions can additionally be identified by a type of surgical robot or robotic arm. The surgical procedure database 622 is populated with data from the procedure module 624, medical professionals, such as surgeons, physicians, nurses, and physical therapists, or from surveys of patient outcomes to evaluate the success of the previous surgical implants or insertion procedures. The surgical procedure database 622 is used by the planning module 626 to determine surgical implant parameters, the timing for inserting the surgical implant components 618, or alternatively, providing another automated action such as maneuvering a surgical tool 154.

Figure 8:
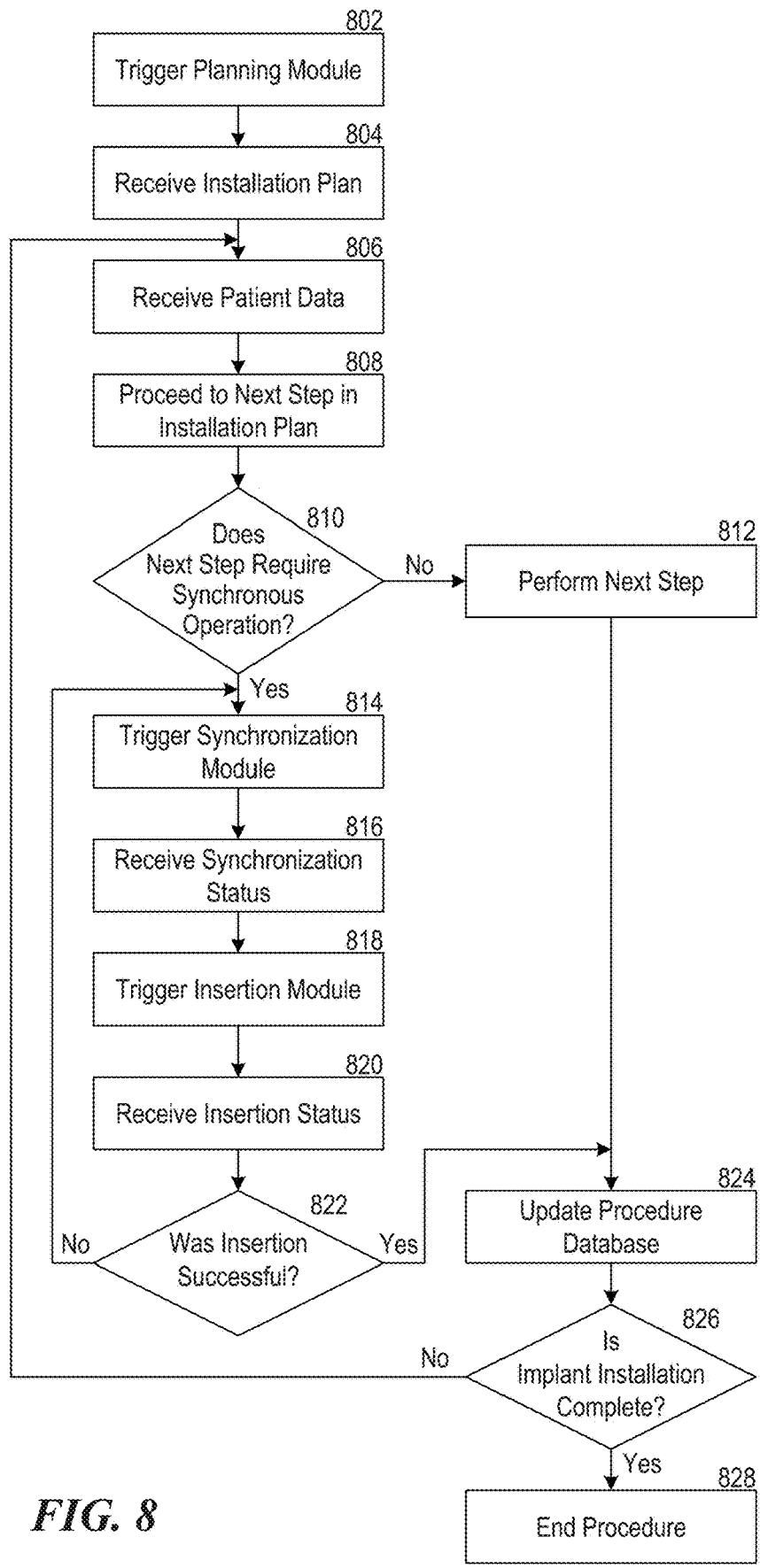
FIG. 8 is a flow diagram illustrating an example process for synchronized placement of surgical implant hardware, in accordance with one or more embodiments.

FIG. 8 is a flow diagram illustrating an example process for synchronized placement of surgical implant hardware, in accordance with one or more embodiments. In some embodiments, the process of FIG. 8 is performed by the procedure module 624. The procedure module 624 is illustrated and described in more detail with reference to FIG. 6. In other embodiments, the process of FIG. 8 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 802, the procedure module 624 triggers the planning module 626 (see FIG. 6) to create an implantation plan for inserting the surgical implant 616 (see FIG. 6) using the synchronous operation of at least two robot arms 604a, 604b connected to the surgical robots 602a, 602b. In embodiments, both robotic arms 604a, 604b are connected to a single surgical robot 604a. In embodiments, each robot arm is connected to a different surgical robot. The surgical robots 602 can be controlled autonomously or by an operator, such as a surgeon. The planning module 626 generates a virtual model of at least a portion of a patient's body, selects at least one implant component 618a (see FIG. 6), places a model of the implant components 618 in the virtual model, and selects surgical tool paths to facilitate insertion of the surgical implant 616. In some embodiments, surgical steps are repeatedly simulated using different tool paths and insertion parameters until a simulated surgical step meets approval criteria, such as user provided criteria based on outcome, time of surgical steps, risk of adverse event, etc. The planning module 626 further selects or generates insertion parameters for controlling at least one surgical robot to insert at least one implant component 618a or perform another action during a surgical procedure. The planning module 626 further generates sequential timing for each action, indicating which actions should be performed at the same time or in the same surgical step.

In step 804, the procedure module 624 receives an implantation plan from the planning module 626. The implantation plan includes a series of actions, each action including sequence and timing data, surgical tool paths, insertion parameters, hardware, or patient parameters, such as acceptable vital sign measurements. Example surgical tools 154 are illustrated and described in more detail with reference to FIG. 1. The implantation plan can include a virtual model of a portion of the patient's body, or design and placement parameters for the surgical implant 616. The implantation plan can include settings for the implant components 618 or listings of surgical tool paths through the virtual model. For example, an implantation plan specifies the synchronized insertion of two screws into a T6 vertebra of a patient, performed autonomously by two surgical robots 102a and 102b. The implantation plan specifies insertion parameters for rotational speed of 10-30 rotations per minute for the end effectors 106a and 106b of the surgical robots 102, the first surgical robot 602a utilizing 1-4 pounds per square inch of axial force, while the second surgical robot 602b utilizing 3-6 pounds per square inch of axial force. Continuing the example, the implantation plan includes insertion parameters specifying an alignment of 10 degrees off the perpendicular from the surface of the bone and 0.5 inches to the left of the spinous process for the first surgical robot 602a. The implantation plan includes insertion parameters specifying an alignment of 15 degrees off the perpendicular from the surface of the bone and 0.5 inches to the right of the spinous process for the second surgical robot 602b.

The procedure module 624 can identify surgical steps to be synchronized, determine timing between synchronized actions of multiple surgical steps, and/or predict outcomes based on synchronization. For example, the procedure module 624 can determine simultaneously performed surgical steps for enhancing implant positioning based on, for example, forces applied to the patient, in-vivo implant assembly, etc. In some procedures, pedicle screws can be simultaneously implanted on opposing sides of a sagittal plane of the patient to limit or reduce motion of the patient's body. In some procedures, implants can be assembled within the patient's body to allow accurate positions of anchors or retention features of the implant. In some procedures, a series of surgical steps for a first implant can be synchronized with a series of surgical steps for a second implant. For example, interbody devices can be expanding while concurrently fixing one or more endplates to the adjacent vertebral bodies. This allows coordination between the expansion process and fixation process.

In step 806, the procedure module 624 receives patient data, such as gender, age, height, weight, allergies, current and prior medical conditions, or any additional clinical information that can impact the outcome of the implantation procedure. The procedure module 624 can further retrieve vital information, such as the patient's blood pressure, heart rate, blood oxygen saturation, respiration rate, etc., from the cloud 620 (see FIG. 6) or a local server. The procedure module 624 can further retrieve baseline vital information from the clinical information or can be retrieved prior to initiating the implantation procedure. The vital information can be continuously or periodically acquired throughout the implantation procedure to monitor the patient's physiological or medical status. For example, the patient data can specify an allergy to latex, chronic osteoporosis, or that the patient's heart rate is 65 beats per minute, blood pressure is 145/105, blood oxygen saturation is 99, and respirations are six breaths per minute.

In step 808, the procedure module 624 executes the next step in the implantation plan. The implantation plan includes surgical steps or actions to be performed by the surgeon or one or more surgical robots 102. The actions can be manual, performed by a surgeon, performed in a hybrid manner, with actions performed by both the surgeon and surgical robots 102, or performed autonomously by the surgical robots 102. The actions can be asynchronous or synchronous, requiring coordination between more than one surgical robot 602 or a surgeon and at least one surgical robot 602. For example, the next step in an implantation plan can be the insertion of two screws to be completed autonomously by the two surgical robots 102a, 102b at the same time.

In step 810, the procedure module 624 determines whether the next step requires the synchronous operation of the two or more surgical robots 102a, 102b or alternatively, an uncoordinated action by a surgeon or surgical robot. Synchronous operation in this context refers to coordinated actions by the surgical robots 102a, 102b to the same time to perform a single surgical step. For example, the surgical robot 602a grips, inserts, and positions the surgical implant component 618a at an implantation site in the patient's body. At the same time, the surgical robot 602b grips, inserts, and positions the surgical implant component 618b at the implantation site in the patient's body, while coordinating with the surgical robot 602a such that there is no physical or timing conflict or contention and that the desired outcome of the surgical step is achieved for inserting the surgical implant 616. In another example, the next step includes the synchronous insertion of two screws to be completed autonomously by two surgical robots 102a, 102b.

An example of an asynchronous surgical step is the making of a 1-inch incision in the muscular tissue of a patient manually by a surgeon. Manual operations can be performed via manual control of a surgical robot 602a by a surgeon, such that the surgical robot 602a does not autonomously perform an action, or alternatively, performs a passive operation to enhance stability by smoothing a surgeon's control inputs. Operations not requiring synchronized operation of two surgical robots 102a, 102b or different robotic arms 104a, 104b can also be performed autonomously by a single surgical robot 602a.

In some embodiments, the first surgical robot 602a performs an asynchronous action on the first surgical implant component 618a at the implantation site in the patient's body in accordance with the implantation plan. For example, in step 810, if the next step is determined to not require synchronization of the surgical robots 102 or robotic arms 104, the procedure module 624 performs the next step operation in step 812. The next step can be performed manually by a surgeon or another member of the surgical team such as a nurse. Alternatively, the next step is performed autonomously by a surgical robot 602a or in a hybrid manner with a surgeon controlling a surgical robot 602b that assists the surgeon, such as by maneuvering the robotic arm 104b and end effector 106b, but otherwise relying on the surgeon to act directly on the patient (e.g., making an incision). For example, the surgeon makes a 1-inch incision in a patient's muscular tissue via manual control of the surgical robot 602b.

In some embodiments, one or more processors of the system of FIG. 6 synchronize first motion of the first surgical robot 602a and second motion of the second surgical robot 602b in accordance with the implantation plan. For example, in step 814, the procedure module 624 triggers the synchronization module 628 (see FIG. 6) to communicate insertion parameters to at least two surgical robots 102 or two different robotic arms 604. In some embodiments, the synchronization module 628 is implemented on the cloud 620 as shown by FIG. 6. In other embodiments, the synchronization module 628 is implemented on the first surgical robot 602a or on the second surgical robot 602b. In other embodiments, an instance of the synchronization module 628 is implemented on each of the first surgical robot 602a and the second surgical robot 602b for the two surgical robots 102 to communicate actions, coordinates of movement, timing constraints, etc., to each other as they perform a synchronous action at the same time or in the same surgical step. The synchronization module 628 can perform pre-synchronous actions in preparation of the synchronous operation of the surgical robots 602 or robotic arms 604. The procedure module 624 can perform the pre-synchronous actions in preparation of the synchronous operation of the surgical robots 602 or robotic arms 604. Alternatively, the surgical robots 602 are prepared for synchronous operation in coordination with a surgeon. For example, the synchronization module 628 moves the first surgical robot 602a into position with its end effector 606a gripping a screw, such that the screw is aligned at 10 degrees off the perpendicular to the surface of the T6 vertebra and 0.5 inches to the left of the spinous process. Continuing the example, the synchronization module 628 moves the second surgical robot 602b into position with its end effector 606b gripping another screw, such that the screw is aligned at 15 degrees off the perpendicular to the surface of the T6 vertebra and 0.5 inches to the right of the spinous process.

In step 816, the procedure module 624 receives a synchronization status of the surgical robots 102 from the synchronization module 628. The synchronization status includes a confirmation that each surgical robot is positioned and in a ready state awaiting a command to begin synchronous operation. For example, the first surgical robot 602a is positioned gripping a screw aligned at 10 degrees off the perpendicular to the surface of the T6 vertebra and 0.5 inches to the left of the spinous process. A second surgical robot 602b is positioned gripping another screw aligned at 15 degrees off the perpendicular to the surface of the T6 vertebra and 0.5 inches to the right of the spinous process.

In step 818, the procedure module 624 triggers the insertion module 630 (see FIG. 6). The insertion module 630 communicates a start command to each of the surgical robots 102 at the same time or in the same surgical step, such that each surgical robot performs its assigned task as determined by the planning module 626 and the synchronization module 628. In some embodiments, one or more processors of the system of FIG. 6 synchronize first motion of the first surgical robot 602a and second motion of the second surgical robot 602b in accordance with the implantation plan. In some embodiments, performing a synchronous action includes sending, by the first surgical robot 602a, information to the second surgical robot 602b during the synchronous action, and moving, by the second surgical robot 602b, the second surgical implant component 618b in response to receiving the information to perform the synchronous action. The information describes the first motion of the first surgical robot 602a. The insertion module 630 further monitors the progress of each surgical robot and the patient's status and returns an insertion status to the procedure module 624 when an anomaly has been detected or when the insertion is complete. For example, the insertion of two screws into a T6 vertebra is successfully completed at the same time or in the same surgical step. Continuing the example, a confirmation of completion is communicated to the procedure module 624 noting a successful insertion status. In another example, the insertion of screws into the T6 vertebra is unsuccessful because the first surgical robot 602a's screw alignment shifted to 16 degrees off the perpendicular, thus exceeding the insertion parameters, and resulting in a suspension of the insertion process and communication of a failed insertion status to the procedure module 624.

In step 820, the procedure module 624 receives the insertion status from the insertion module 630. The insertion status includes either a confirmation that the insertion process was successfully completed by each surgical robot in accordance with nominal insertion parameters or a notification that the insertion process failed and was suspended due to at least one insertion parameter exceeding an acceptable range of insertion parameters determined by the planning module 626 and the synchronization module 628. The nominal insertion parameters refer to parameters within the acceptable range of insertion parameters. For example, the insertion status can indicate the successful insertion of two screws into the T6 vertebra. In another example, the procedure module 624 receives a notification that the insertion process failed and that the insertion process was suspended before completing.

In step 822, the procedure module 624 determines whether the insertion was successful. If the insertion was successful, the procedure module 624 update the surgical procedure database 622 in step 824. If the insertion was not successful, the procedure module 624 returns to step 814 and triggers the synchronization module 628 to determine updated insertion parameters for the insertion process. The procedure module 624 or the synchronization module 628 perform pre-synchronous operations in preparation for another attempt at the synchronous insertion operation. For example, having failed the first insertion attempt, the procedure module 624 returns to step 814 and prompts the synchronization module 628 to update the insertion parameters for the first surgical robot 602a, which was originally aligned at 10% off the perpendicular but failed the insertion process because the alignment shifted to 16% off the perpendicular. Continuing the example, the first surgical robot 602a adjusts its alignment to 12% and changes the rotational speed to 20-50 rotations per minute.

In step 824, the procedure module 624 updates the surgical procedure database 622 (see FIG. 6) with data from the previously completed actions. The data specifies the actions completed, the insertion parameters and timing information, or patient data, including vital information before, during, or after the insertion process. For example, the procedure module 624 updates the surgical procedure database 622, indicating that two screws were inserted into either side of the spinous process of the T6 vertebra at the same time or in the same surgical step by two surgical robots 102. The first surgical robot 602a used an alignment of 10 degrees off the perpendicular from the surface of the bone at a location 0.5 inches to the left of the spinous process and applied 3 pounds per square inch of axial force while inserting a screw with 20 rotations per minute. The second surgical robot 602b used an alignment of 15 degrees off the perpendicular from the surface of the bone at a location 0.5 inches to the right of the spinous process and applied 5 pounds per square inch of axial force while inserting a screw with 20 rotations per minute. Continuing the example, the insertion of each screw commenced at the same time or in the same surgical step as the second surgical robot 602b, and completing a second before the first surgical robot 602a. During the insertion process, the patient maintained a heart rate of 65 beats per minute, blood pressure of 145/105, blood oxygen saturation of 99, and respirations of six breaths per minute.

In step 826, the procedure module 624 determines whether installation of the implant 116 is complete. The implant 116 installation is complete when all required surgical implant components 618 have been inserted and no further steps remain to be performed by either a surgeon or any of the surgical robots 102 according to the implantation plan. If the implantation is not complete, the procedure module 624 returns to step 806 and receives updated patient data to include at least the patient's disposition and additionally vital information, such as heart rate and blood pressure. In step 826, the procedure module 624 terminates the implantation procedure if the implant installation is complete.

Figure 9:
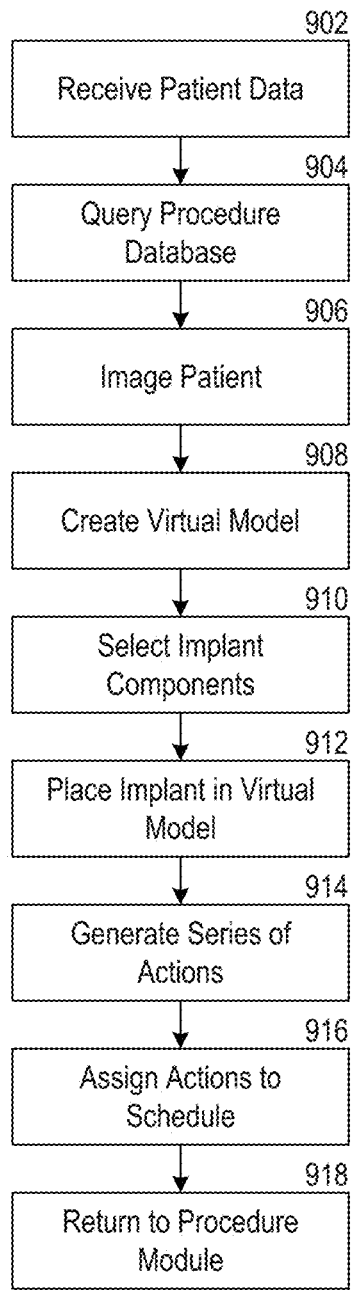
FIG. 9 is a flow diagram illustrating an example process for synchronized placement of surgical implant hardware, in accordance with one or more embodiments.

FIG. 9 is a flow diagram illustrating an example process for synchronized placement of surgical implant hardware, in accordance with one or more embodiments. In some embodiments, the process of FIG. 9 is performed by the planning module 626. The planning module 626 is illustrated and described in more detail with reference to FIG. 6.

In other embodiments, the process of FIG. 9 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 902, the planning module 626 receives patient data from the installation module 624 (see FIG. 6). The patient data includes any of gender, age, height, weight, allergies, current or prior medical conditions, or any additional clinical information that can impact the outcome of the implantation procedure. Patient data can additionally include vital information, such as the patient's blood pressure, heart rate, blood oxygen saturation, respiration rate, etc. For example, the patient data can include the patient's vital information, including heart rate of 65 beats per minute, blood pressure of 145/105, blood oxygen saturation of 99, or respirations of six breaths per minute. Continuing the example, in addition, the planning module 626 receives data indicating that the patient is female and has osteoporosis.

In step 904, the planning module 626 queries the surgical procedure database 622 (see FIG. 6) for data from historical implantation procedures. The data describing the previous implantation procedures includes a series of steps or actions taken during the previous procedures. The previous steps or actions can specify previous surgical tool paths, previous surgical implant component paths, and insertion parameters used, such as the direction and speed of movement of a surgical tool 154 (see FIG. 1). The previous steps or actions can specify operational parameters, such as rotational speed, axial force exerted by the surgical tool 154, or tool alignment. Each previous step or action additionally specifies a sequence order and timing, describing when the step or action should be completed, in what order, and the expected duration of each step or action. For example, a step can include the automated insertion of a screw into the bone of a patient by a surgical robot 602a. The data retrieved by the planning module 626 from the surgical procedure database 622 can specify the previous insertion parameters (e.g., rotational speed of 10-30 rotations per minute, axial force of 1-5 pounds per square inch, and an alignment angle of 15 degrees off the perpendicular from the surface of the bone). Continuing the example, the screw insertion is to occur after the surface of the bone has been prepared and before the installation of at least one rod. Further, the step of inserting the screw is to be performed at the same time of the insertion of a second screw.

In some embodiments, each surgical step or robotic action further includes multiple steps or actions required to achieve an objective. For example, a surgical step can include the actions of aligning a screw to 15 degrees off the perpendicular prior to rotating the screw at a rate of 20 rotations per minute and then applying a force of 4 pounds per square inch. Some actions within a surgical step can include synchronous (at the same time or in the same surgical step) and asynchronous actions. For example, the alignment of two screws by two surgical robots 102 can occur asynchronously prior to the synchronized insertion of both screws. The planning module 626 can determine benefits of performing asynchronous or synchronized actions. For example, the planning module 626 can determine whether applying screws at the same time would result in an excessive moment to be applied to the patient's body. If so, the planning module 626 can determine alternative steps to be formed at the same time. A user can set criteria (e.g., parameters, thresholds, outcomes, target time for surgical steps, target time for surgical procedure, etc.) for the synchronization analysis. The planning module 626 can also use machine-trained models to analyze previous outcomes to prioritize outcomes, such as reducing length of surgery, implant positioning accuracy, etc. A physician can prioritize outcomes based on, among other things, the patient's health.

In step 906, the planning module 626 images a portion of the body of the patient using at least one imaging device 614 (see FIG. 6) such MRI, computer aided tomography, or ultrasound (see FIG. 1). The imaging includes at least the implantation site receiving the implant 616 and the surrounding area in the patient's body. Alternatively, the imaging can include the entirety of the patient's body. For example, the planning module 626 images a portion of the body of the patient using MRI, such that multiple images are taken representing slices at varying depths.

In step 908, the planning module 626 generates a virtual model of at least a portion of the body of the patient using the images captured of the patient by the imaging device 614. The virtual model can be two-dimensional or three-dimensional. Other embodiments can include a virtual model having a fourth dimension of time, such that the model is animated with the movement of the body over a period of time. For example, multiple MRI slices are layered to create a three-dimensional virtual model of the patient's spine and surrounding tissues in preparation of performing a spinal 360 fusion procedure via the insertion of the implant 616 fusing three vertebrae together.

In some embodiments, implanting the surgical implant 616 (see FIG. 6) in the patient's body includes performing in vivo assembly of the surgical implant 616 from the first surgical implant component 618a and the second surgical implant component 618b. The in vivo assembly uses a first cannula in the patient's body for the first surgical robot 602a and a second cannula in the patient's body for the second surgical robot 602b. For example, in step 910, the planning module 626 selects the surgical implant components 618 (see FIG. 6) that make up the implant 616. The implant 616 can include a single surgical implant component 618a or an assembly of multiple surgical implant components 618a, 618b. An assembly can be inserted as a single unit or can require insertion in multiple discrete pieces to result in the final surgical implant. Use of an assembly can improve functionality of the implant 616, such as allowing for articulation or flexibility, or can facilitate the insertion of the implant 616, such that the assembled implant 616 is more rigid with little or no flexibility. Selection of the surgical implant components 618 further includes selecting the material that each surgical implant component is made of. For example, the surgical implant components 618 of a spinal implant 616 include six screws, each with a head known as a "tulip" to receive one of two rods and two plates to join the two rods together to prevent movement relative to one another. Continuing the example, all the implant components 618 are made of titanium.

In step 912, the planning module 626 virtually places a model of at least one surgical implant 616 in or on the virtual model of the patient using simulations and CAD (see FIGS. 4B-5). A model of the implants 616 are placed in the virtual model to mimic or simulate an ideal physical scenario by a surgeon or a surgical robot. For example, a model of a spinal implant 616 is inserted into a three-dimensional model of a patient's thoracic spine to simulate fusing three vertebrae to one another. In this example, the spinal implant 616 includes at least two screws inserted an inch into each vertebra, one on either side of the spinous process, and perpendicular to the surface of the vertebrae. Additionally, two rods located on either side of the spinous process are each secured to a screw on its respective side of the spinous process via a tulip. Continuing the example, two plates connect the two rods to each another to prevent the rods from moving relative to one another.

In some embodiments, synchronizing the first motion (of the first surgical robot 602a) and the second motion (of the second surgical robot 602b) includes generating, by one or more processors of the system of FIG. 6, a path for the first surgical robot 602a based on the second motion and a coordinated timing for inserting the surgical implant 616 in the patient's body by the first surgical robot 602a and the second surgical robot 602b. For example, in step 914, the planning module 626 generates a sequence of actions, each specifying surgical tool paths, paths for surgical implant components, or insertion parameters to act as instructions for a surgeon or the surgical robots to aid the insertion of the surgical implant components 618. The surgical tool paths can also be manually defined or generated by a computer algorithm, such that the surgical tool path avoids nervous tissues, rigid bone structures, blood vessels, or other organs or tissues. Sometimes, anatomical features need to be displaced during a surgical procedure, e.g., a portion of the bone is removed or an organ is moved to access a surgical site. A tool path is typically generated for each surgical step or robotic action and movement within the patient's body. For example, a surgical step or robotic action can specify paths for surgical tools for creating incisions, managing bleeding, maneuvering, or installing the surgical implant components 618 in the patient's body. For example, a specified path for a surgical tool 154 (see FIG. 1) or a surgical implant component 618b can be associated with moving a rod for installation along the spine of a patient into the incision site and parallel to the spine until the rod is in position alongside the spinous process and above a set of screws. Continuing the example, another path can be associated with engaging the rod with a tulip on a head of each screw.

In step 914, the planning module 626 further generates insertion parameters to control the insertion of the surgical implant components 618. The insertion parameters can specify, for example, a rate of movement of a surgical implant component 618a through the patient's body, an orientation of the surgical implant component 618a, or a force that should be applied to engage a rod with screws. For example, a surgical implant component 118a is moved within the patient's body by pushing a rod lengthwise into an incision towards a surgical site until the rod is in position. In this example, the rod is pushed at a rate not to exceed two inches per minute. When the rod is positioned above the screws the rod is intended to engage, a force perpendicular to the rod is applied, not to exceed ten pounds per square inch until the rod engages the screw heads.

In step 916, the planning module 626 assigns the generated surgical steps or robotic actions to a schedule by generating a sequential order number for each surgical step or robotic action and additionally approximating a time duration for each surgical step or robotic action. In some embodiments, the sequential order number is unique for each robotic action or movement. In other embodiments, multiple robotic actions or movements have the same order number, indicating that the actions should be completed at the same time, in the same surgical step, or in a synchronized manner instead of as in multiple discrete steps. The time duration is the amount of time each robotic action or movement should take.

The time duration can specify complex timing rules for the discrete parts of a robotic action, such as aligning a surgical implant component 618a or a surgical tool 154 (see FIG. 1), initiating the rotation of a rotary surgical tool, applying an axial force to a surgical tool 154, etc. For example, an action of inserting a first screw by the first surgical robot 602a is assigned a sequential order number of 23. Upon receiving a start command, the first surgical robot 602a begins rotating the screw at a speed of 20 rotations per minute, and after two seconds, applies up to three pounds per square inch of axial force for no more than ten seconds. Continuing the example, another action of inserting a second screw by the second surgical robot 602b is also assigned a sequential order number of 23. Upon receiving a start command, the second surgical robot 602b begins rotating the second screw at a speed of 25 rotations per minute. After two seconds, the second surgical robot 602b applies up to five pounds per square inch of axial force for no more than ten seconds. The actions directing the first surgical robot 602a and the second surgical robot 602b both have the order number of 23, indicating that the actions are to be completed in a synchronized manner. Synchronized actions can specify an asynchronous action to be completed prior to the synchronized actions. For example, a synchronized action by the first surgical robot 602a can specify that the first surgical robot 602a is to perform a pre-synchronized action of aligning a screw to an angle of ten degrees off the perpendicular with the surface of the T6 vertebra and 0.5 inches to the left of the spinous process. A synchronized action by the second surgical robot 602b can specify that the second surgical robot 602b is to perform a pre-synchronized action of aligning the screw to 15 degrees off the perpendicular with the surface of the T6 vertebra and 0.5 inches to the right of the spinous process.

In step 918, the planning module 626 returns control to the procedure module 624 when the surgical implant components 618 have been selected. Models of the surgical implant components 618 have been placed in a virtual model of the patient, and at least one tool path, insertion parameters, and timing constraints have been generated. The implantation plan is thus generated, specifying the surgical implant components 618, their placement, the surgical tool paths, insertion parameters, and timing constraints.

Figure 10:
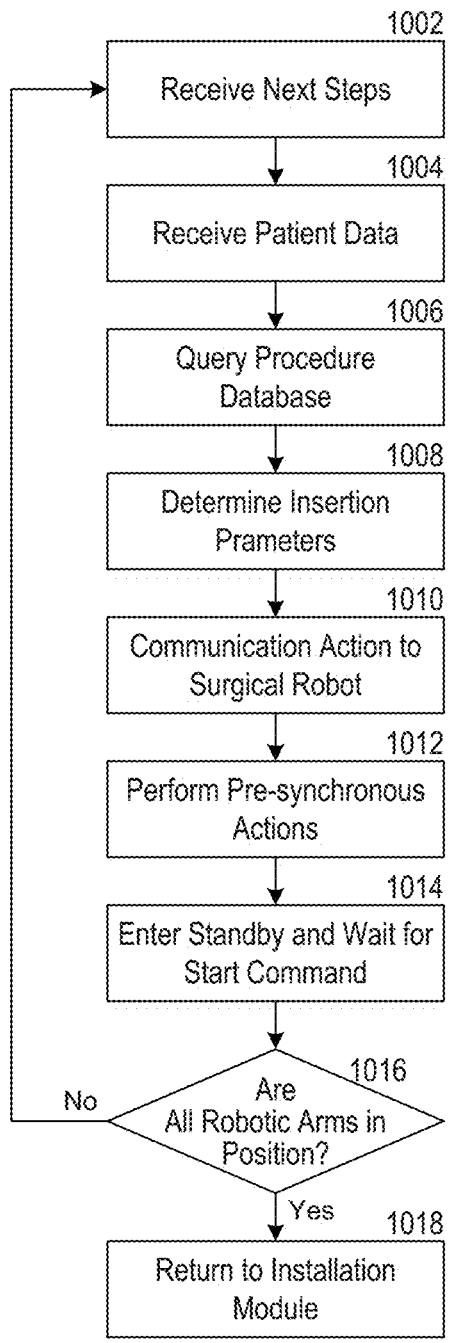
FIG. 10 is a flow diagram illustrating an example process for synchronized placement of surgical implant hardware, in accordance with one or more embodiments.

FIG. 10 is a flow diagram illustrating an example process for synchronized placement of surgical implant hardware, in accordance with one or more embodiments. In some embodiments, the process of FIG. 10 is performed by the synchronization module 628. The synchronization module 628 is illustrated and described in more detail with reference to FIG. 6. In other embodiments, the process of FIG. 10 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 1002, the synchronization module 628 receives information specifying the next steps in an implantation plan from the procedure module 624 (see FIG. 6). The next steps include at least two robotic actions to be completed in a synchronized manner. For example, a first action is the insertion of a first screw by a first surgical robot 602a 0.5 inches left of the spinous process of the T6 vertebra. A second action is the insertion of a second screw by a second surgical robot 602b 0.5 inches to the right of the spinous process of the T6 vertebra. The insertion of the first screw by the first surgical robot 602a and the insertion of the second screw by the second surgical robot 602b is to be performed at the same time or in the same surgical step, i.e., in a synchronized manner.

In step 1004, the synchronization module 628 receives patient data from the procedure module 624. The patient data includes any of gender, age, height, weight, allergies, current and prior medical conditions, or other clinical information that can impact the outcome of the implantation procedure. The patient data can additionally include vital information, such as the patient's blood pressure, heart rate, blood oxygen saturation, respiration rate, etc. For example, a patient's data includes the patient's vital information, such as a heart rate of 65 beats per minute, a blood pressure of 145/105, a blood oxygen saturation of 99, or respirations of six breaths per minute. In addition, the synchronization module 628 receives patient data indicating that the patient is female and has osteoporosis.

In step 1006, the synchronization module 628 queries the surgical procedure database 622 (see FIGS. 6-7) for data from historical surgical implant installation procedures. The data describing the previously performed installation procedures specifies the previous surgical steps or robotic actions taken during previous implantation procedures. The surgical steps or robotic actions further specify one or more surgical tool paths and previous insertion parameters, such as a direction and speed of movement of a surgical tool 153 (see FIG. 1). The surgical steps or robotic actions further specify previous operational parameters, such as rotational speed, axial force exerted by the tool, or tool alignment. The surgical steps or robotic actions further specify previous operational parameters associated with the previously installed surgical implant components.

In some embodiments, each surgical step or robotic action further specifies a sequence order and timing describing when the step or action should be completed, in what order, and the expected duration of each step or action. For example, a surgical step is the automated insertion of a screw into the bone of a patient by a surgical robot 602a. In this example, the surgical step specifies the insertion parameters of rotational speed of 10-30 rotations per minute, an axial force of 1-5 pounds per square inch, and an alignment angle of 15 degrees off the perpendicular from the surface of the bone. Continuing the example, the screw insertion is to occur after the surface of the bone has been prepared and before the insertion of at least one rod. Further, the step of inserting a screw is to occur together with the insertion of a second screw. In some embodiments, each surgical step or robotic action can include multiple smaller steps or actions required to achieve an objective. A surgical step can be specified in a hierarchical manner. For example, a Level 1 surgical step can include one or more Level 2 surgical steps. Each Level 2 surgical step can include one or more Level 3 robotic actions. For example, a surgical step includes the robotic actions of aligning a screw to 15 degrees off the perpendicular prior to rotating the screw at a rate of 20 rotations per minute and then applying a force of 4 pounds per square inch. Some robotic actions within a surgical step can include synchronous and asynchronous components. For example, the alignment of two screws by two surgical robots 102a, 102b occurs asynchronously prior to the synchronized insertion of both screws. In some embodiments, an implantation plan is specified recursively, such that invoking a first surgical step passes control to other steps and then the first surgical step itself directly or indirectly.

In step 1008, the synchronization module 628 determines the insertion parameters (sometimes referred to a current insertion parameters) to be used during the insertion of the surgical implant components 618 in the patient's body. In a first scenario, the insertion parameters used are the insertion parameters generated by the planning module 626 (see FIG. 6). In a second scenario, the planning module 626 does not generate insertion parameters and the insertion parameters are generated by the synchronization module 628. In a third scenario, after a previous attempt to insert the surgical implant components 618 fails, the insertion parameters are regenerated to accommodate an anomaly that caused the failure of the previous insertion attempt. The synchronization module 628 modifies the current insertion parameters using a regression model. For example, the synchronization module 628 compares the current insertion parameters generated (e.g., by the planning module 626) to previous insertion parameters stored in the surgical procedure database 622 (see FIG. 6) and determines an offset. The synchronization module 628 applies the offset to determine new insertion parameters and recursively modify the insertion parameters using the data in the surgical procedure database 622.

In some embodiments, the insertion parameters include paths for at least one surgical tool 154 (see FIG. 1) or a surgical implant component 618a. For example, first insertion parameters are generated for the first surgical robot 602a. The insertion parameters include an orientation of a first screw at 10 degrees off center and 0.5 inches to the left of the spinous process of the T6 vertebra, and further a rotational speed not to exceed 20 rotations per minute and an axial force not to exceed 4 pounds per square inch. Continuing the example, second insertion parameters are generated for the second surgical robot 602b to achieve the synchronous insertion of the first screw and a second screw into the T6 vertebra. The second insertion parameters include an orientation of the second screw at 15 degrees off center and 0.5 inches to the right of the spinous process of the T6 vertebra, a rotational speed not to exceed 30 rotations per minute, and an axial force not to exceed 5 pounds per square inch.

In step 1010, the synchronization module 628 sends information describing at least a first robotic action and first insertion parameters to the first surgical robot 602a. The communication is performed by the communications interface 612a (that can be wireless or wired) and other components such as the network 314 and network adapter 312 (see FIG. 3). In addition, the synchronization module 628 sends information describing at least a second robotic action and second insertion parameters to the second surgical robot 602b. The communication is performed by the communications interface 612b and other components, such as the network 314 and network adapter 312. In some embodiments, the information describing both actions and both sets of insertion parameters is sent to both surgical robots 102, such that the surgical robots 102 coordinate amongst themselves. Similarly, data describing robotic actions and insertion parameters can be sent to any additional surgical robots. For example, the system of FIG. 6 uses the wired communications interfaces 112 to communicate with the surgical robots 102.

In step 1012, based on information sent by the synchronization module 628 to each surgical robot 602a, the each surgical robot 602a performs one or more pre-synchronous (sometimes referred to as asynchronous) actions independently of the surgical robot 602b in an asynchronous manner in preparation of one or more synchronized (sometimes referred to as synchronous) actions to be performed. In some embodiments, the first surgical robot 602a performs the asynchronous action independently of the second surgical robot 602b. The asynchronous action includes at least one of moving, by a robotic arm 604a of the first surgical robot 602a, the first surgical implant component 618a towards the implantation site in the patient's body for performing the synchronous action, or aligning, by the robotic arm 604a, the first surgical implant component 618a at the implantation site for performing the synchronous action. For example, a pre-synchronous action includes moving and aligning a screw by a first surgical robot 602 so that the screw is aligned 10 degrees off the perpendicular with the surface of the T6 vertebra with the tip of the screw contacting the surface of the bone at 0.5 inches to the left of the spinous process. In another example, a pre-synchronous action includes moving and aligning a screw by the second surgical robot 602b, such that the screw is aligned 15 degrees off the perpendicular with the surface of the T6 vertebra with the tip of the screw contacting the surface of the bone at 0.5 inches to the right of the spinous process.

In step 1014, the synchronization module 628 enters a standby state and waits for a start command before initiating the synchronized insertion process according to the insertion parameters. In some embodiments, the standby state includes a stationary position with the surgical robots 102 configured with the insertion parameters and timing of each element of the insertion process, such that the insertion process can begin upon receiving a start command. The synchronous insertion process can include a delay to be executed prior to beginning the insertion process if indicated by the insertion parameters and timing data. The start command can be transmitted by one of the surgical robots 602a to each of the other surgical robots 602b. Alternatively, the surgical robots 602 can each receive a start command from an external source, such as a local terminal or from the cloud 620 (see FIG. 6). In other embodiments, a start command is manually transmitted from a surgeon. The transmission can be a discrete action, initiating the insertion process or the start command can be triggered when the surgeon performs another action, such as initiating the insertion of a screw.

In some embodiments, a the system of FIG. 6 includes multiple surgical robots 602 selected based on the surgical procedures (e.g., open procedures, minimally invasive procedures, etc.) and/or tasks to be performed. For example, the surgical robot 602a can be configured to autonomously perform particular surgical procedures (e.g., robotic surgical procedures) or a portion thereof (e.g., physician-assisted surgical procedures). The surgical robot 602b can be configured to perform auxiliary procedures or tasks, including pre-operative tasks, tasks associated with nurses (e.g., scrub nurse tasks, circulating nurse tasks, etc.), and/or surgical-related tasks. For example, the surgical robot 602b can be configured to perform robotic anesthetics, sedation, ventilation, vital monitoring, or the like. The configuration of the system of FIG. 6 and the surgical robots 602 can be selected based on the particular surgical actions (e.g., physician actions, nurse actions, technician tasks, etc.) to be robotically performed. In some embodiments, the surgical robots 602 perform different types of surgical procedures. For example, the surgical robot 602a can perform an open procedure while the surgical robot 602b performs a minimally invasive procedure. In other embodiments, each of the surgical robots 602*a*, 602*b* performs either an open procedure or a minimally invasive procedure.

The system of FIG. 6 can be programmed to perform surgical tasks based on one or more simulations and additional surgical robots can be added to the system. This allows flexibility to configure the surgical system to robotically perform surgical steps associated with a surgeon, nurse steps, technician steps, and/or surgical-related steps or tasks, including monitoring of operating room robots and/or staff, the patient, equipment, surgeons, supplies, or the like. The system of FIG. 6 can select the schedule, operating room 102 (see FIG. 1), surgical staff, surgical robots, surgical resources (e.g., computing resources, network resources, etc.), and/or equipment to be used based on the particular surgical procedure to be performed.

In some embodiments, a synchronous action is performed in a surgical step. Prior to performing the synchronous action, one or more processors of the system of FIG. 6 determine that the first surgical robot 602*a* and the second surgical robot 602*b* are required for the surgical step by the implantation plan. The one or more processors determine that the first surgical robot 602*a* and the second surgical robot 602*b* have completed one or more asynchronous actions required by the implantation plan. The one or more processors determine that the first surgical robot 602*a* and the second surgical robot 602*b* are located at positions required by the implantation plan. For example, in step 1016, the synchronization module 628 determines whether the surgical robots 102 and the robotic arms 104 are in position. The surgical robots 102 are in position when all surgical robots 102 with actions having an order number matching the order number of the current step have completed their pre-synchronous actions, have been configured with the insertion parameters for their respective actions, and have entered a standby state awaiting a start command. For example, the first surgical robot 602*a* and the second surgical robot 602*b* are each in their respective positions and are in a standby state waiting for a start command to initiate the synchronized insertion of two screws into the T6 vertebra of the patient. If the surgical robots 102 are not in position, the synchronization module 628 returns to step 1002 and receives next actions for any remaining surgical robot that is not yet in position.

In step 1016, the synchronization module 628 passes control to the procedure module 624 when all surgical robots 102 are in position in a standby state awaiting a start command.

Figure 11:
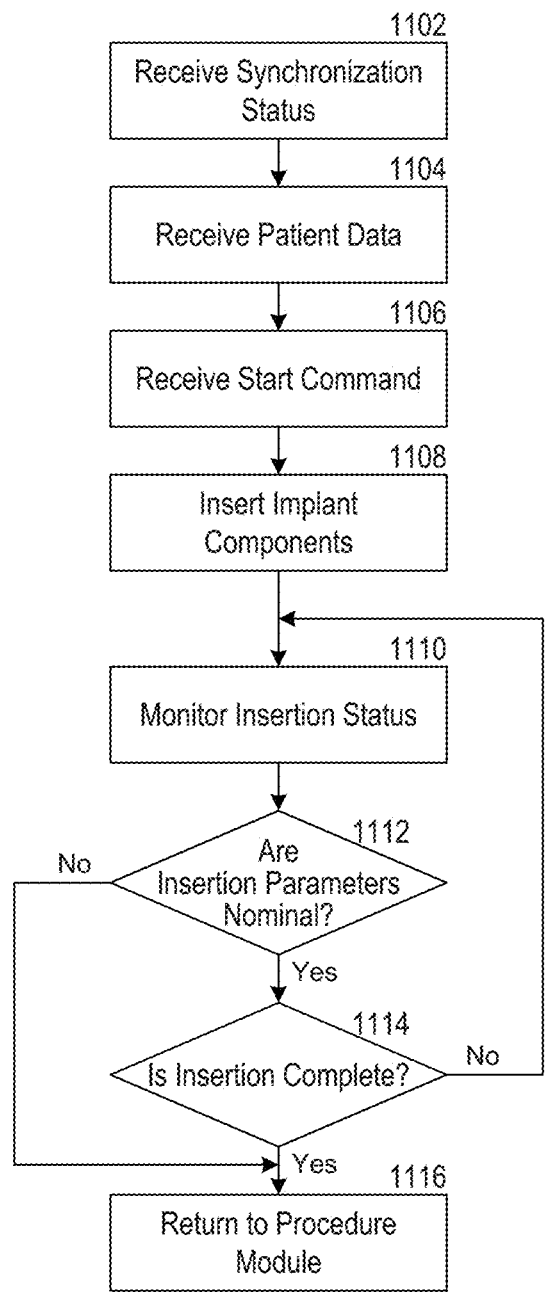
FIG. 11 is a flow diagram illustrating an example process for synchronized placement of surgical implant hardware, in accordance with one or more embodiments.

FIG. 11 is a flow diagram illustrating an example process for synchronized placement of surgical implant hardware, in accordance with one or more embodiments. In some embodiments, the process of FIG. 11 is performed by the insertion module 630. The insertion module 630 is illustrated and described in more detail with reference to FIG. 6. In other embodiments, the process of FIG. 11 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 1102, the insertion module 630 receives a synchronization status from the procedure module 624 (see FIG. 6). The synchronization status includes a confirmation that each surgical robot 602*a* is positioned and in a ready state awaiting a command to begin synchronous operation. For example, the first surgical robot 602*a* is positioned gripping a first screw aligned 10 degrees off the perpendicular to the surface of the T6 vertebra and 0.5 inches to the left of the spinous process. The second surgical robot 602*b* is positioned gripping a second screw aligned 15 degrees off the perpendicular to the surface of the T6 vertebra and 0.5 inches to the right of the spinous process.

In step 1104, the insertion module 630 receives patient data from the procedure module 624. The patient data includes any of gender, age, height, weight, allergies, current and prior medical conditions, or other additional clinical information that can impact the outcome of the installation procedure. The patient data can additionally include vital information, such as a patient's blood pressure, heart rate, blood oxygen saturation, respiration rate, etc. For example, the patient data indicates the patient's vital information including a heart rate of 65 beats per minute, a blood pressure of 145/105, a blood oxygen saturation of 99, and respirations of six breaths per minute.

In step 1106, the insertion module 630 generates and sends a start command to one or more other components of the system of FIG. 6. In some embodiments, the insertion module 630 is implemented within the surgical robot 602*a*, the surgical robot 602*b*, or a local terminal. For example, the start command is received by each surgical robot 602*a* and can further be transmitted by any of a surgical robot 602*a*, a local terminal, the cloud 620, a surgeon providing a direct command via a control panel or terminal, or via a surgeon initiating an action such as beginning to insert a screw into the bone of a patient. In another example, the start command is transmitted by a surgeon via a local terminal. The surgeon reviews the alignment of each robotic arm 104*a* and selects a command to initiate the action which is transmitted to and received by both the first surgical robot 602*a* and the second surgical robot 602*b*.

In step 1108, based on information from the insertion module 630, the surgical implant components 618 are inserted as indicated by the insertion parameters. In some embodiments, one or more processors of the system of FIG. 6 synchronize first motion of the first surgical robot 602*a* and second motion of the second surgical robot 602*b* in accordance with the implantation plan. In some embodiments, the first surgical robot 602*a* and the second surgical robot 602*b* perform a synchronous action to insert the surgical implant 616 in the patient's body in accordance with the insertion parameters. The synchronous action includes controlling the first surgical implant component 618*a* by the first surgical robot 602*a* synchronously with the second motion, and controlling the second surgical implant component 618*b* by the second surgical robot 602*b* synchronously with the first motion. For example, the surgical implant components 618 are inserted at the same time or in the same surgical step by both the first surgical robot 602*a* and the second surgical robot 602*b*. For example, the first surgical robot 602*a* inserts a first screw into the T6 vertebra at 0.5 inches left of the spinous process by rotating the first screw at a rate of 20 rotations per minute and applying an axial force of 3 pounds per square inch while the second surgical robot 602*b* inserts a second screw into the T6 vertebra at 0.5 inches right of the spinous process by rotating the second screw at a rate of 25 rotations per minute and applying an axial force of 4 pounds per square inch.

In step 1110, the insertion module 630 monitors the insertion progress of each of the surgical implant components 618 being inserted by the first surgical robot 602*a* and the second surgical robot 602*b*. The insertion module 630 monitors the insertion progress including the current position of each implant component 618a or surgical tool 154 (see FIG. 1), and a rate of movement or other parameters described in the insertion parameters for each surgical robot 602a. For example, the insertion module 630 determines that a first screw being inserted by the first surgical robot 602a has reached a depth of 0.5 inches with a target depth of 1 inch and the first screw is rotating at a rate of 20 rotations per minute with an axial force of 3 pounds per square inch being applied to the screw, while a second screw being inserted by the second surgical robot 602b has reached a depth of 0.75 inches with a target depth of 1 inch and the second screw is rotating at a rate of 25 rotations per minute with an axial force of 4 pounds per square inch being applied to the second screw. A surgeon can additionally monitor the insertion progress by observing the surgical robots' actions and/or current insertion parameters.

In some embodiments, one or more processors of the system of FIG. 6 determine that a position or alignment of at least one of the first surgical implant component 618a or the second surgical implant component 618b violates the insertion parameters based on monitoring the synchronous action. The first surgical robot 602a and the second surgical robot 602b abort insertion of the surgical implant 616 in the patient's body in response to determining that the position or alignment violates the insertion parameters. For example, in step 1112, the insertion module 630 determines whether the insertion parameters are nominal or within the ranges specified by the insertion parameters generated by the planning module 626 or the synchronization module 628. Alternatively, a surgeon can monitor the insertion parameters and determine whether the insertion parameters are acceptable regardless of whether they are within the insertion parameter ranges previously specified.

For example, the current insertion parameters for the insertion of a first screw into the T6 vertebra by the first surgical robot 602a reveal that the first screw has reached a depth of 0.5 inches with a target depth of 1 inch and the screw is rotating at a rate of 20 rotations per minute with an axial force of 3 pounds per square inch being applied to the screw. Further, the insertion module 630 determines that the synchronous insertion of a second screw by the second surgical robot 602b has reached a depth of 0.75 inches with a target depth of 1 inch and the screw is rotating at a rate of 25 rotations per minute with an axial force of 4 pounds per square inch being applied to the second screw. If the insertion parameters are not nominal and an anomaly is detected, first surgical robot 602a and the second surgical robot 602b abort the insertion process and return control to the procedure module 624 with an insertion status indicating that the insertion process failed. In another example, the alignment of a screw being inserted into the T6 vertebra by the first surgical robot 602a is found to have deviated from the desired 10 degrees off the perpendicular with the surface of the bone to 15 degrees off the perpendicular. Because this deviation in alignment exceeds the insertion parameters, the insertion process is aborted and both the first surgical robot 602a and the second surgical robot 602b stop the insertion of their respective screws.

In step 1114, the insertion module 630 determines whether the insertion of the implant components 118 is complete. The insertion is complete if the final position or depth installation parameter is met for each implant component 118a being inserted during the insertion process. Alternatively, the insertion is complete when the end position of a surgical tool 154 or other end result is achieved. The insertion can alternatively be determined to be complete when a surgeon determines that the insertion is complete and inputs a completion confirmation to at least one surgical robot 602a. The command is similarly transmitted to all surgical robots 102. For example, the insertion is indicated to be complete when a first screw inserted by the first surgical robot 602a has reached a final depth of 1 inch and a second screw inserted by the second surgical robot 602b has also reached a final depth of 1 inch.

In step 1116, the insertion module 630 returns control to the installation module 624 when the insertion is complete. The insertion module 630 provides an insertion status to the installation module 624 either confirming that the insertion has been completed or indicating that an anomaly was detected, and the insertion failed because the insertion process was aborted either by a surgical robot 602a or the surgeon.

The functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

What is claimed is:

1. A method comprising:
   generating, by one or more processors of a surgical system, an implantation plan for implanting a surgical implant in a patient's body, the implantation plan comprising insertion parameters for controlling a first surgical robot and a second surgical robot of the surgical system, wherein the surgical implant comprises a first surgical implant component and a second surgical implant component;
   performing, by the first surgical robot, an asynchronous action on the first surgical implant component at the implantation site in the patient's body in accordance with the implantation plan;
   synchronizing, by the one or more processors, first motion of the first surgical robot and second motion of the second surgical robot in accordance with the implantation plan; and
   performing, by the first surgical robot and the second surgical robot, a synchronous action to position the surgical implant within the patient's body in accordance with the insertion parameters, wherein the synchronous action comprises:
   controlling the first surgical implant component by the first surgical robot synchronously with the second motion; and
   controlling the second surgical implant component by the second surgical robot synchronously with the first motion.

2. The method of claim 1, wherein performing the synchronous action comprises:
   sending, by the first surgical robot, information to the second surgical robot during the synchronous action, the information describing the first motion of the first surgical robot; and
   moving, by the second surgical robot, the second surgical implant component in response to receiving the information to perform the synchronous action.

3. The method of claim 1, wherein the first surgical robot performs the asynchronous action independently of the second surgical robot, and wherein the asynchronous action comprises at least one of:
   moving, by a robotic arm of the first surgical robot, the first surgical implant component towards the implantation site in the patient's body for performing the synchronous action; or
   aligning, by the robotic arm, the first surgical implant component at the implantation site for performing the synchronous action.

4. The method of claim 1, wherein the synchronous action is performed in a surgical step, the method further comprising:
   prior to performing the synchronous action:
      determining, by the one or more processors, that the first surgical robot and the second surgical robot are required for the surgical step by the implantation plan;
      determining, by the one or more processors, that the first surgical robot and the second surgical robot have completed one or more asynchronous actions required by the implantation plan; and
      determining, by the one or more processors, that the first surgical robot and the second surgical robot are located at positions required by the implantation plan.

5. The method of claim 1, wherein synchronizing the first motion and the second motion comprises generating, by the one or more processors, a path for the first surgical robot based on the second motion and a coordinated timing for inserting the surgical implant in the patient's body by the first surgical robot and the second surgical robot.

6. The method of claim 1, wherein implanting the surgical implant in the patient's body comprises performing in vivo assembly of the surgical implant from the first surgical implant component and the second surgical implant component, the in vivo assembly using a first cannula in the patient's body for the first surgical robot and a second cannula in the patient's body for the second surgical robot.

7. The method of claim 1, further comprising:
   determining, by the one or more processors, that a position or alignment of at least one of the first surgical implant component or the second surgical implant component violates the insertion parameters based on monitoring the synchronous action; and
   aborting, by the first surgical robot and the second surgical robot, insertion of the surgical implant in the patient's body in response to determining that the position or alignment violates the insertion parameters.

8. A surgical system comprising:
   one or more computer processors; and
   a non-transitory computer-readable storage medium storing computer instructions, which when executed by the one or more computer processors, cause the surgical system to:
   generate an implantation plan for implanting a surgical implant in a patient's body, the implantation plan comprising insertion parameters for controlling a first surgical robot and a second surgical robot of the surgical system, wherein the surgical implant comprises a first surgical implant component and a second surgical implant component;
   perform, by the first surgical robot, an asynchronous action on the first surgical implant component at the implantation site in the patient's body in accordance with the implantation plan;
   synchronize first motion of the first surgical robot and second motion of the second surgical robot in accordance with the implantation plan; and
   perform, by the first surgical robot and the second surgical robot, a synchronous action to position the surgical implant in the patient's body in accordance with the insertion parameters, wherein the computer instructions to perform the synchronous action cause the surgical system to:
   control the first surgical implant component by the first surgical robot synchronously with the second motion; and
   control the second surgical implant component by the second surgical robot synchronously with the first motion.

9. The surgical system of claim 8, wherein the computer instructions to perform the synchronous action cause the surgical system to:
   send, by the first surgical robot, information to the second surgical robot during the synchronous action, the information describing the first motion of the first surgical robot; and
   move, by the second surgical robot, the second surgical implant component in response to receiving the information to perform the synchronous action.

10. The surgical system of claim 8, wherein the first surgical robot performs the asynchronous action independently of the second surgical robot, and wherein the computer instructions to perform the asynchronous action cause the surgical system to:

move, by a robotic arm of the first surgical robot, the first surgical implant component towards the implantation site in the patient's body for performing the synchronous action; or align, by the robotic arm, the first surgical implant component at the implantation site for performing the synchronous action.

11. The surgical system of claim 8, wherein the synchronous action is performed in a surgical step, the computer instructions further causing the surgical system to:

prior to performing the synchronous action:

determine that the first surgical robot and the second surgical robot are required for the surgical step by the implantation plan;

determine that the first surgical robot and the second surgical robot have completed one or more asynchronous actions required by the implantation plan; and determine that the first surgical robot and the second surgical robot are located at positions required by the implantation plan.

12. The surgical system of claim 8, wherein the computer instructions to synchronize the first motion and the second motion cause the surgical system to generate a path for the first surgical robot based on the second motion and a coordinated timing for inserting the surgical implant in the patient's body by the first surgical robot and the second surgical robot.

13. The surgical system of claim 8, wherein the computer instructions to implant the surgical implant in the patient's body cause the surgical system to perform in vivo assembly of the surgical implant from the first surgical implant component and the second surgical implant component, the in vivo assembly using a first cannula in the patient's body for the first surgical robot and a second cannula in the patient's body for the second surgical robot.

14. The surgical system of claim 8, wherein the computer instructions further cause the surgical system to:

determine that a position or alignment of at least one of the first surgical implant component or the second surgical implant component violates the insertion parameters based on monitoring the synchronous action; and abort, by the first surgical robot and the second surgical robot, insertion of the surgical implant in the patient's body in response to determining that the position or alignment violates the insertion parameters.

15. A computer-implemented method comprising:

positioning, by a first surgical robot of a surgical system, a first surgical implant component in a patient's body according to an implantation plan for implanting a surgical implant at an implantation site in a patient, the surgical implant comprising the first surgical implant component and a second surgical implant component;

positioning, by a second surgical robot of the surgical system, the second surgical implant component in the patient's body; and performing, by the first surgical robot and the second surgical robot, a synchronous action to assemble the surgical implant within the patient's body from the first surgical implant component and the second surgical implant component in accordance with insertion parameters of the implantation plan.

16. The computer-implemented method of claim 15, further comprising:

monitoring the insertion parameters to determine an offset from a surgical procedure database;

applying the offset to determine new insertion parameters by recursively modifying the insertion parameters.

17. The computer-implemented method of claim 15, wherein performing the synchronous action comprises at least one of:

controlling, by the first surgical robot, a path of the first surgical implant component in the patient's body;

controlling, by the second surgical robot, an orientation of the second surgical implant component in the patient's body; or controlling, by the first surgical robot, an axial force applied to the first surgical implant component in the patient's body.

18. The computer-implemented method of claim 15, further comprising generating a path for a surgical tool of the surgical system in a virtual model of the patient's body to virtually insert the surgical implant in the virtual model.

19. The computer-implemented method of claim 15, further comprising performing a virtual robotic surgical procedure for the surgical system according to the implantation plan to virtually insert a model of the surgical implant at the implantation site.

20. The computer-implemented method of claim 15, further comprising:

virtually simulating one or more surgical steps of the implantation plan using a three-dimension model generated using real-time patient data; and analyzing the virtual simulation to determine the insertion parameters.

\* \* \* \* \*